(12) United States Patent
Livak et al.

(10) Patent No.: US 8,809,238 B2
(45) Date of Patent: Aug. 19, 2014

(54) PROBE BASED NUCLEIC ACID DETECTION

(75) Inventors: Kenneth J. Livak, San Jose, CA (US); Stacey N. Meyers, San Francisco, CA (US); Jun Wang, Palo Alto, CA (US); Xiaohui Wang, Foster City, CA (US)

(73) Assignee: Fluidigm Corporation, South San Francisco, CA (US)

( * ) Notice: Subject to any disclaimer, the term of this patent is extended or adjusted under 35 U.S.C. 154(b) by 0 days.

(21) Appl. No.: 13/467,933

(22) Filed: May 9, 2012

(65) Prior Publication Data
US 2013/0045881 A1    Feb. 21, 2013

Related U.S. Application Data

(60) Provisional application No. 61/484,198, filed on May 9, 2011.

(51) Int. Cl.
     *G01N 21/64*     (2006.01)
     *C40B 30/04*     (2006.01)
     *C12Q 1/68*      (2006.01)

(52) U.S. Cl.
     CPC .................................. *C12Q 1/6818* (2013.01)
     USPC ............................................ 506/9; 435/6.11

(58) Field of Classification Search
None
See application file for complete search history.

(56) References Cited

U.S. PATENT DOCUMENTS

| | | | |
|---|---|---|---|
| 6,540,895 B1 | 4/2003 | Spence et al. |
| 6,885,982 B2 | 4/2005 | Harris et al. |
| 6,951,632 B2 | 10/2005 | Unger et al. |
| 7,042,649 B2 | 5/2006 | Quake et al. |
| 7,059,348 B2 | 6/2006 | Nat |
| 7,062,418 B2 | 6/2006 | Lee et al. |
| 7,097,809 B2 | 8/2006 | Van Dam et al. |
| 7,161,736 B2 | 1/2007 | Legrand et al. |
| 7,192,629 B2 | 3/2007 | Lammertink et al. |
| 7,217,367 B2 | 5/2007 | Huang et al. |
| 7,232,109 B2 | 6/2007 | Driggs et al. |
| 7,248,413 B2 | 7/2007 | Quake et al. |
| 7,262,923 B2 | 8/2007 | Quake et al. |
| 7,279,146 B2 | 10/2007 | Nassef |
| 7,291,512 B2 | 11/2007 | Unger |
| 7,294,503 B2 | 11/2007 | Quake et al. |
| 7,368,163 B2 | 5/2008 | Huang et al. |
| 7,442,556 B2 | 10/2008 | Manger et al. |
| 7,476,363 B2 | 1/2009 | Unger et al. |
| 7,526,741 B2 | 4/2009 | Lee et al. |
| 7,604,965 B2 | 10/2009 | McBride et al. |
| 7,615,620 B2 | 11/2009 | Robinson |
| 7,666,361 B2 | 2/2010 | McBride et al. |
| 7,678,547 B2 | 3/2010 | Eyal et al. |
| 7,691,333 B2 | 4/2010 | McBride et al. |
| 7,749,737 B2 | 7/2010 | McBride et al. |
| 7,792,345 B2 | 9/2010 | Taylor et al. |
| 7,815,868 B1 | 10/2010 | Jones et al. |
| 7,820,427 B2 | 10/2010 | Unger et al. |
| 7,833,708 B2 | 11/2010 | Enzelberger et al. |
| 7,837,946 B2 | 11/2010 | McBride et al. |
| 2004/0180377 A1 | 9/2004 | Manger et al. |
| 2005/0053952 A1 | 3/2005 | Hong et al. |
| 2005/0239084 A1 | 10/2005 | Nadeau et al. |
| 2006/0172408 A1 | 8/2006 | Quake et al. |
| 2006/0233674 A1 | 10/2006 | Nelson |
| 2006/0281183 A1 | 12/2006 | Sun et al. |
| 2007/0134807 A1 | 6/2007 | Bao et al. |
| 2007/0224617 A1 | 9/2007 | Quake et al. |
| 2007/0248971 A1 | 10/2007 | Maerkl et al. |
| 2008/0050283 A1 | 2/2008 | Chou et al. |
| 2008/0075380 A1 | 3/2008 | Dube et al. |
| 2008/0108063 A1 | 5/2008 | Lucero et al. |
| 2008/0129736 A1 | 6/2008 | Sun et al. |
| 2008/0176211 A1 | 7/2008 | Spence et al. |
| 2008/0223721 A1 | 9/2008 | Cohen et al. |
| 2008/0230387 A1 | 9/2008 | McBride et al. |
| 2008/0264863 A1 | 10/2008 | Quake et al. |
| 2008/0274493 A1 | 11/2008 | Quake et al. |
| 2008/0281090 A1 | 11/2008 | Lee et al. |
| 2008/0292504 A1 | 11/2008 | Goodsaid et al. |
| 2009/0018195 A1 | 1/2009 | Balagadde |

(Continued)

FOREIGN PATENT DOCUMENTS

| | | |
|---|---|---|
| EP | 1726664 B1 | 1/2010 |
| WO | 01/67369 A2 | 9/2001 |

(Continued)

OTHER PUBLICATIONS

Solinas, A. et al. 2001. Duplex Scorpion primers in SNP analysis and FRET applications. Nucleic Acids Research, vol. 29, No. 20, e96, pp. 1-9.

(Continued)

*Primary Examiner* — Catherine Hibbert
(74) *Attorney, Agent, or Firm* — Kilpatrick Townsend & Stockton LLP

(57) ABSTRACT

The invention provides a method for detecting a target nucleotide sequence by tagging the nucleotide sequence with a nucleotide tag, providing a probe oligonucleotide with a melting temperature Tm1, comprising a regulatory sequence and a nucleotide tag recognition sequence; incorporating the probe oligonucleotide into the tagged polynucleotide in a polynucleotide amplification reaction, providing a regulatory oligonucleotide with a melting temperature Tm2, comprising a sequence segment that is at least partially complementary to the regulatory sequence, amplifying the tagged target nucleic acid sequence in a PCR amplification reaction using the probe oligonucleotide as a primer, and detecting the amplification product; wherein Tm1 and Tm2 are higher than the annealing temperature associated with the polynucleotide amplification reaction.

20 Claims, 1 Drawing Sheet

(56) References Cited

U.S. PATENT DOCUMENTS

| | | | |
|---|---|---|---|
| 2009/0069194 A1 | 3/2009 | Ramakrishnan | |
| 2009/0142236 A1 | 6/2009 | Unger et al. | |
| 2009/0147918 A1 | 6/2009 | Fowler et al. | |
| 2009/0168066 A1 | 7/2009 | Hansen et al. | |
| 2009/0239308 A1 | 9/2009 | Dube et al. | |
| 2009/0291435 A1 | 11/2009 | Unger et al. | |
| 2010/0086916 A1* | 4/2010 | Mao et al. | 435/6 |
| 2010/0104477 A1 | 4/2010 | Liu et al. | |
| 2010/0120018 A1 | 5/2010 | Quake et al. | |
| 2010/0120077 A1 | 5/2010 | Daridon | |
| 2010/0154890 A1 | 6/2010 | Maerkl et al. | |
| 2010/0166608 A1 | 7/2010 | Quan et al. | |
| 2010/0171954 A1 | 7/2010 | Quake et al. | |
| 2010/0183481 A1 | 7/2010 | Facer et al. | |
| 2010/0184202 A1 | 7/2010 | McBride et al. | |
| 2010/0187105 A1 | 7/2010 | Unger et al. | |
| 2010/0196892 A1 | 8/2010 | Quake et al. | |
| 2010/0197522 A1 | 8/2010 | Liu et al. | |
| 2010/0200782 A1 | 8/2010 | Unger et al. | |
| 2010/0230613 A1 | 9/2010 | Pieprzyk et al. | |
| 2010/0263732 A1 | 10/2010 | Hansen et al. | |
| 2010/0263757 A1 | 10/2010 | Fernandes et al. | |
| 2010/0311060 A1 | 12/2010 | Facer et al. | |
| 2010/0320364 A1 | 12/2010 | Unger et al. | |

FOREIGN PATENT DOCUMENTS

| | | |
|---|---|---|
| WO | 02/30946 A1 | 4/2002 |
| WO | 2007/033385 A2 | 3/2007 |
| WO | 2007/044091 A2 | 4/2007 |
| WO | 2008/043046 A2 | 4/2008 |
| WO | 2009/100449 A1 | 8/2009 |
| WO | 2010/011852 A1 | 1/2010 |
| WO | 2010/017210 A1 | 2/2010 |
| WO | 2010/077618 A1 | 7/2010 |
| WO | 2011/053790 A2 | 5/2011 |

OTHER PUBLICATIONS

Li, Q. et al. 2002. A new class of homogeneous nucleic acid probes based on specific displacement hybridization. Nucleic Acids Research, vol. 30, No. 2, e5, pp. 1-9.

Zhang Y. et al. 2003. A novel real-time quantitative PCR method using attached universal template probe. Nucleic Acids Research, vol. 31, No. 20, e123, pp. 1-8.

Bengra, C. et al. 2002. Genotyping of Essential Hypertension Single-Nucleotide Polymorphisms by a Homogeneous PCR Method with Universal Energy Transfer Primers. Clinical Chemistry, vol. 48, No. 12, pp. 2131-2140.

Cheng, J. et al. 2004. Real-time PCR genotyping using displacing probes. Nucleic Acids Research, vol. 32, No. 7, e61, pp. 1-10.

Marras, S. et al. 2002. Efficiencies of fluorescence resonance energy transfer and contact-mediated quenching in oligonucleotide probes. Nucleic Acids Research, vol. 30, No. 21, e122, pp. 1-8.

Allen Am. et al. 2011. Transcript-specific, single-nucleotide polymorphism discovery and linkage analysis in hexaploid bread wheat (*Triticum aestivum* L.) Plant Biotechnology Journal, vol. 9, No. doi: 10.1111/j.1467-7652.2011.00628.x.

Li, J. et al. 2006. Antiprimer Quenching-Based Real-Time PCR and Its Application to the Analysis of Clinical Cancer Samples. Clinical Chemistry 52(4): 624-633; together with data supplements figures S1 to S5 and legends.

Fiandaca, M. J. et al. 2001. Self-Reporting PNA/DNA Primers for PCR Analysis. Genome Research 11: 609-613.

Wallace, R. B et al. 1979. Hybridization of synthetic oligodeoxynucleoticies to fX174 DNA: the effect of single base pair mismatch. Nucleic Acids Res. 6, 3543-3557.

Sambrook, J. et al. 1989. In Molecular Cloning: A Laboratory Manual, 2 edition, vol. II, pp. 11, 46-11.47. Cold Spring Harbor Laboratory Press, New York.

SantaLucia, J., Jr, 2007 Physical Principles and Visual-OMP Software for Optimal PCR Design, Methods in Molecular Biology: PCR Primer Design, Anton Yuryev, Ed., Humana Press, Totowa, New Jersey, Methods Mol. Biol. 402, 3-34.

Bommarito, S., et al. 2000 Thermodynamic parameters for DNA sequences with dangling ends, Nucleic Acids Res. 28, 1929-1934.

*Statement of Opposition* to EP 172664 dated Oct. 26, 2010, 24 pages.

*Further Submissions of the Opponent* filed in Opposition to EP 172664 on Aug. 30, 2012, 22 pages.

Li et al., "Anti-primer quenching-based real-time PCR for simplex or multiplex DNA quantification and single-nucleotide polymorphism genotyping", Nature Protocols, Feb. 22, 2007, p. 50-58, vol. 2, No. 1.

Livak, K. J., "Allelic discrimination using fluorogenic probes and the 5' nuclease assay", Genetic Analysis: Biomolecular Engineering, 1999, p. 143-149, vol. 14, No. 5-6.

Nazarenko, I., "Homogenous Detection of Nucleis Acids Using Self-Quenching Polymerase Chain Reachtion primers Labeled with a Single Fluorophone (LUX™ Primers)", Methods in Molecular Biology, 2006, p. 95-114, vol. 335.

\* cited by examiner

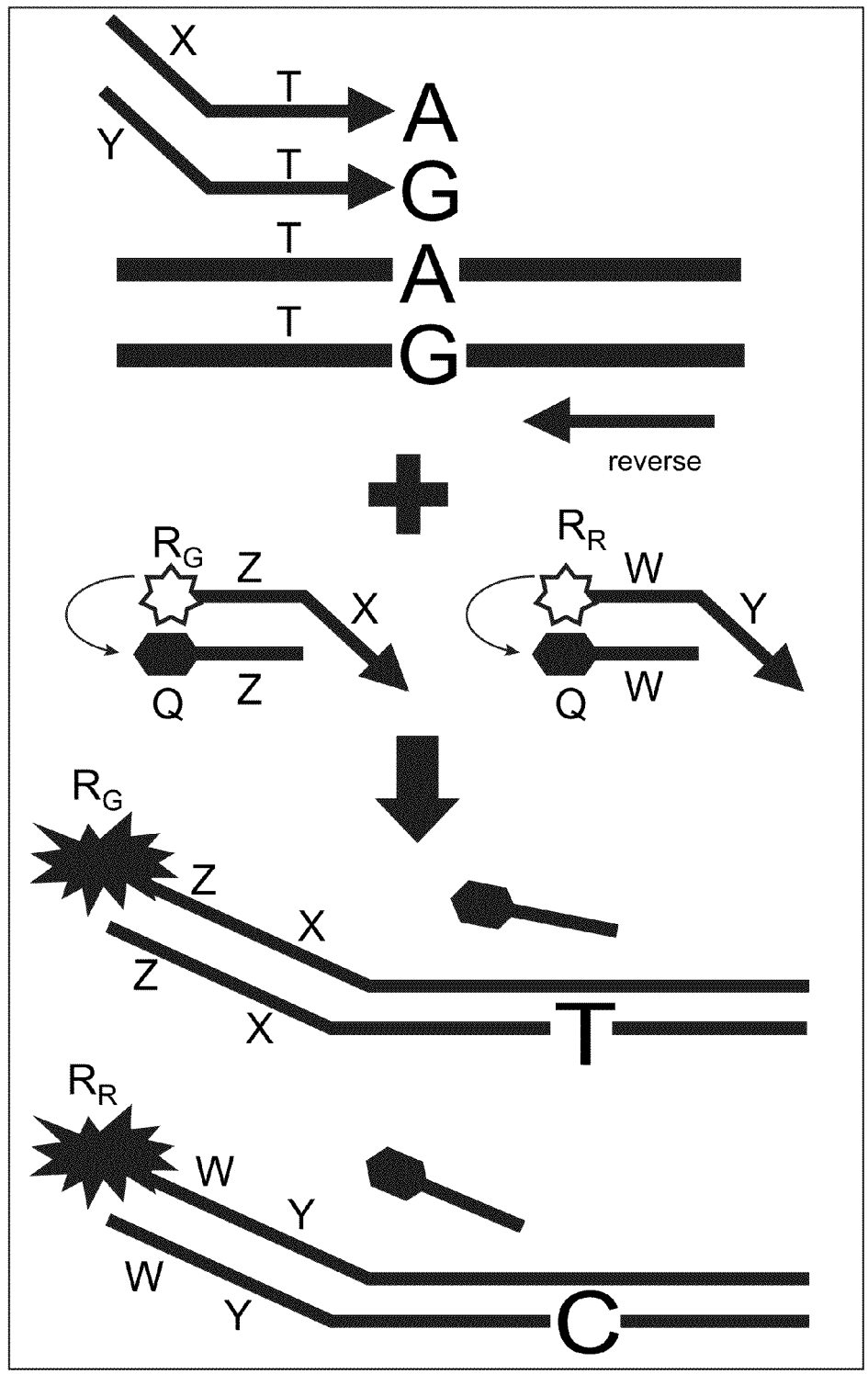

PROBE BASED NUCLEIC ACID DETECTION

CROSS REFERENCE TO RELATED APPLICATIONS

This application claims priority to U.S. provisional application No. 61/484,198, filed May 9, 2011, the entire contents of which are incorporated herein by reference.

REFERENCE TO A "SEQUENCE LISTING," A TABLE, OR A COMPUTER PROGRAM LISTING APPENDIX SUBMITTED AS AN ASCII TEXT FILE

The Sequence Listing written in file 85665-838605_ST25.TXT, created on May 9, 2012, 13,706 bytes, machine format IBM-PC, MS-Windows operating system, is hereby incorporated by reference in its entirety for all purposes.

FIELD OF THE INVENTION

The invention relates to a PCR-based detection system suitable for nucleotide polymorphism (SNP) genotyping and other genetic assays.

BACKGROUND OF THE INVENTION

Fluorescent reporter molecule—quencher molecule pairs have been incorporated onto probe oligonucleotides in order to monitor biological events based on the fluorescent reporter molecule and quencher molecule being separated or brought within a minimum quenching distance of each other. For example, probes have been developed where the intensity of the reporter molecule fluorescence increases due to the separation of the reporter molecule from the quencher molecule. Probes have also been developed which lose their fluorescence because the quencher molecule is brought into proximity with the reporter molecule. These reporter—quencher molecule pair probes have been used to monitor hybridization assays and nucleic acid amplification reactions, especially polymerase chain reactions (PCR), by monitoring either the appearance or disappearance of the fluorescence signal generated by the reporter molecule.

One particularly important application for probes including a reporter—quencher molecule pair is their use in nucleic acid amplification reactions, such as polymerase chain reactions (PCR), to detect the presence and amplification of a target nucleic acid sequence. In general, nucleic acid amplification techniques have opened broad new approaches to genetic testing and DNA analysis. Arnheim and Erlich, Ann. Rev. Biochem., 61: 131-156 (1992). PCR, in particular, has become a research tool of major importance with applications in, for example, cloning, analysis of genetic expression, DNA sequencing, genetic mapping and drug discovery. Arnheim and Erlich, Ann. Rev. Biochem., 61: 131-156 (1992); Gilliland et al., Proc. Natl. Acad. Sci., 87: 2725-2729 (1990); Bevan et al., PCR Methods and Applications, 1: 222-228 (1992); Green et al., PCR Methods and Applications, 1: 77-90 (1991); Blackwell et al., Science, 250: 1104-1110 (1990).

Accordingly, a need exists for probes which exhibit distinguishable fluorescence characteristics when hybridized and not hybridized to a target nucleic acid sequence. A further need exists for probes where the reporter molecule and quencher molecule are positioned on detection pairs such that the quencher molecule can effectively quench the fluorescence of the reporter molecule. A further need exists for probes which are efficiently synthesized. A further need exists for a detection method, wherein few synthesized probes can be used in a large number of assays. Yet a further need exists for a detection method with high specificity. A further need exists for proximity based quenching positioning the reporter molecule and quencher molecule on the detection pairs such that the reporter and quencher molecules are sufficiently close to each other upon sequence specific hybridization.

These and further objectives are provided by the probes and methods of the present invention.

SUMMARY OF THE INVENTION

In one aspect, the invention provides a method for detecting a target nucleotide sequence comprising:

a) tagging the target nucleotide sequence with a nucleotide tag sequence, thereby producing a tagged target nucleic acid sequence;

b) providing a probe oligonucleotide comprising a nucleotide tag recognition sequence complementary to the nucleotide tag sequence and a regulatory sequence 5' to the nucleotide tag recognition sequence, wherein said probe oligonucleotide comprises a first label and has a melting temperature Tm1;

c) amplifying the tagged target nucleic acid sequence in a PCR amplification reaction using the probe oligonucleotide as a primer, wherein said PCR amplification reaction is characterized by an annealing temperature Ta;

wherein the PCR amplification reaction is carried out in the presence of a regulatory oligonucleotide comprising a sequence segment that is complementary to the regulatory sequence, wherein said regulatory oligonucleotide comprises a second label and has a melting temperature Tm2; and d) detecting the product of the PCR amplification reaction;

wherein the first label and the second label constitute a fluorescent reporter/quencher pair; and wherein Tm1 and Tm2 are both higher than Ta.

In an embodiment, the tag sequence is incorporated into the tagged target nucleic acid sequence using a PCR reaction.

In an embodiment, the nucleotide tag recognition sequence is exactly complementary to the nucleotide tag sequence. In an embodiment, the regulatory oligonucleotide comprises a sequence segment that is exactly complementary to regulatory sequence. In an embodiment, the regulatory oligonucleotide has a length in the range of 15-45 nucleotides. In an embodiment, Ta is in the range of 55-62° C. In an embodiment, Ta is in the range of 60-64° C. In an embodiment, Ta is in the range of 60° C.-62° C. In some embodiments, Tm1 is at least 25° C. higher than the annealing temperature (Ta). In some embodiments, Tm2 is at least at least 2° C., at least 3° C., at least 4° C., at least 5° C., or at least 10° C. higher than the annealing temperature (Ta). In some embodiments Tm2 is in the range of 60-75° C. In some embodiments, Tm1 and Tm2 are calculated by the formula: $T_m(° C.)=4(G+C)+2(A+T)$.

In some embodiments the PCR amplification reaction is carried out in a reaction volume greater than 500 nL, or greater than 1 uL. For example, in some embodiments the PCR amplification reactions are carried out in a multiwell plate comprising 96-1536 wells. In some embodiments, Ta is about 57° C.

In some embodiments the PCR amplification reaction is carried out in a reaction volume less than 100 nL. In some embodiments the PCR amplification reaction is carried out in a microfluidic device. In some embodiments Ta is about 60° C.

In certain embodiments, Ta is the yielding annealing temperature. In some embodiments the PCR amplification reaction comprises at least 20 cycles at the annealing temperature (Ta).

BRIEF DESCRIPTION OF THE DRAWINGS

FIG. 1 illustrates the use of the present assay for genotyping. T=target sequence, or complement; X, Y=tag sequence, or complement, $R_G$, $R_R$=reporters, Q=quencher(s), z, w=regulatory sequence, or complement.

DETAILED DESCRIPTION

A. Definitions

Terms used in the claims and specification are defined as set forth below unless otherwise specified. These terms are defined specifically for clarity, but all of the definitions are consistent with how a skilled person in the art would understand these terms.

It also noted that as used herein and in the appended claims, the singular forms "a," "an," and "the" include the plural reference unless the context clearly dictates otherwise. Thus, for example, a reference to "a cell" is a reference to one or more cells and equivalents thereof known to those skilled in the art.

As used herein, "immobilized" means insolubilized or comprising, attached to or operatively associated with an insoluble, partially insoluble, colloidal, particulate, dispersed, suspended and/or dehydrated substance or a molecule or solid phase comprising or attached to a solid support.

As used herein, "solid support" refers to a composition comprising an immobilization matrix such as but not limited to, insolubilized substance, solid phase, surface, substrate, layer, coating, woven or nonwoven fiber, matrix, crystal, membrane, insoluble polymer, plastic, glass, biological or biocompatible or bioerodible or biodegradable polymer or matrix, microparticle or nanoparticle. Solid supports include, for example and without limitation, monolayers, bilayers, commercial membranes, resins, matrices, fibers, separation media, chromatography supports, polymers, plastics, glass, mica, gold, beads, microspheres, nanospheres, silicon, gallium arsenide, organic and inorganic metals, semiconductors, insulators, microstructures and nanostructures. Microstructures and nanostructures may include, without limitation, microminiaturized, nanometer-scale and supramolecular probes, tips, bars, pegs, plugs, rods, sleeves, wires, filaments, and tubes.

The term "adjacent," when used herein to refer two nucleotide sequences in a nucleic acid, can refer to nucleotide sequences separated by 0 to about 20 nucleotides, more specifically, in a range of about 1 to about 10 nucleotides, or sequences that directly abut one another.

The term "nucleic acid" refers to a nucleotide polymer, and unless otherwise limited, includes analogs of natural nucleotides that can function in a similar manner (e.g., hybridize) to naturally occurring nucleotides. Unless otherwise limited "nucleic acids" can include, in addition to the standard bases adenine, cytosine, guanine, thymine and uracil, various naturally occurring and synthetic bases (e.g., inosine), nucleotides and/or backbones.

The term nucleic acid includes any form of DNA or RNA, including, for example, genomic DNA; complementary DNA (cDNA), which is a DNA representation of mRNA, usually obtained by reverse transcription of messenger RNA (mRNA) or by amplification; DNA molecules produced synthetically or by amplification; and mRNA.

The term nucleic acid encompasses double- or triple-stranded nucleic acids, as well as single-stranded molecules. In double- or triple-stranded nucleic acids, the nucleic acid strands need not be coextensive (i.e, a double-stranded nucleic acid need not be double-stranded along the entire length of both strands).

The term nucleic acid also encompasses any chemical modification thereof, such as by methylation and/or by capping. Nucleic acid modifications can include addition of chemical groups that incorporate additional charge, polarizability, hydrogen bonding, electrostatic interaction, and functionality to the individual nucleic acid bases or to the nucleic acid as a whole. Such modifications may include base modifications such as 2-position sugar modifications, 5-position pyrimidine modifications, 8-position purine modifications, modifications at cytosine exocyclic amines, substitutions of 5-bromo-uracil, backbone modifications, unusual base pairing combinations such as the isobases isocytidine and isoguanidine, and the like.

More particularly, in certain embodiments, nucleic acids, can include polydeoxyribonucleotides (containing 2-deoxy-D-ribose), polyribonucleotides (containing D-ribose), and any other type of nucleic acid that is an N- or C-glycoside of a purine or pyrimidine base, as well as other polymers containing normucleotidic backbones, for example, polyamide (e.g., peptide nucleic acids (PNAs)) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. The term nucleic acid also encompasses linked nucleic acids (LNAs), which are described in U.S. Pat. Nos. 6,794,499, 6,670,461, 6,262,490, and 6,770,748, each of which is incorporated herein by reference.

The nucleic acid(s) can be derived from a completely chemical synthesis process, such as a solid phase-mediated chemical synthesis, from a biological source, such as through isolation from any species that produces nucleic acid, or from processes that involve the manipulation of nucleic acids by molecular biology tools, such as DNA replication, PCR amplification, reverse transcription, or from a combination of those processes.

The term "target nucleic acids" is used herein to refer to particular nucleic acids to be detected in the methods of the invention.

As used herein the term "target nucleotide sequence" refers to a nucleotide sequence of interest, such as, for example, the amplification product obtained by amplifying a target nucleic acid or the cDNA produced upon reverse transcription of an RNA target nucleic acid. In the case of RNA, the target nucleotide sequence can substitute thymidine (T) for uracil (U).

As used herein, the term "complementary" refers to the capacity for precise pairing between two nucleotides. I.e., if a nucleotide at a given position of a nucleic acid is capable of hydrogen bonding with a nucleotide of another nucleic acid, then the two nucleic acids are considered to be complementary to one another at that position. A "complement" may be an exactly or partially complementary sequence. Complementarity between two single-stranded nucleic acid molecules may be "partial," in which only some of the nucleotides bind, or it may be complete when total complementarity exists between the single-stranded molecules. The degree of complementarity between nucleic acid strands has significant effects on the efficiency and strength of hybridization between nucleic acid strands. Two sequences that are partially complementary may have, for example, at least 90% identity, or at least 95%, 96%, 97%. 98%, or 99% identity sequence over a sequence of at least 7 nucleotides, more typically in the range of 10-30 nucleotides, and often over a sequence of at least 14-25 nucleotides. It will be understood that the 3' base of a primer sequence will desirably be perfectly complementary to corresponding bases of the target nucleic acid sequence to allow priming to occur.

"Specific hybridization" refers to the binding of a nucleic acid to a target nucleotide sequence in the absence of substantial binding to other nucleotide sequences present in the hybridization mixture under defined stringency conditions. Those of skill in the art recognize that relaxing the stringency of the hybridization conditions allows sequence mismatches to be tolerated. In particular embodiments, hybridizations are carried out under stringent hybridization conditions.

"$T_m$" refers to "melting temperature", which is the temperature at which a population of double-stranded nucleic acid molecules becomes half-dissociated into single strands. The $T_m$ of a single stranded oligonucleotide, as used herein, refers to the $T_m$ of a double stranded molecule comprising the oligonucleotide and its exact complement. Reporters or quenchers are not included in the determination of $T_m$. As used herein, $T_m$ may be determined by calculation. Specifically, the $T_m$ of an oligonucleotide may be a calculated $T_m$ according to the equation: "$T_m$ (° C.)=4(G+C)+2(A+T)" (Thein and Wallace, 1986, in Human genetic disorders, p 33-50, IRL Press, Oxford UK, incorporated herein by reference).

The term "oligonucleotide" is used to refer to a nucleic acid that is relatively short, generally shorter than 200 nucleotides, more particularly, shorter than 100 nucleotides, most particularly, shorter than 50 nucleotides. Typically, oligonucleotides are single-stranded DNA molecules. Oligonucleotides used in the invention can be chemically modified. Chemical modifications can equip the oligonucleotides with additional functionalities, such as chemical activity, affinity or protection from degradations, e.g. by nucleases.

The term "primer" refers to an oligonucleotide that is capable of hybridizing (also termed "annealing") with a nucleic acid and serving as an initiation site for nucleotide (RNA or DNA) polymerization under appropriate conditions (e.g., in the presence of four different nucleoside triphosphates and an agent for polymerization, such as DNA or RNA polymerase or reverse transcriptase) in an appropriate buffer and at a suitable temperature. The appropriate length of a primer depends on the intended use of the primer, but primers are typically at least 7 nucleotides long and, more typically range from 10 to 30 nucleotides, or even more typically from 15 to 30 nucleotides, in length. Other primers can be somewhat longer, e.g., 30 to 60 nucleotides long. In this context, "primer length" refers to the portion of an oligonucleotide or nucleic acid that hybridizes to a complementary "target" sequence and primes nucleotide synthesis. Short primer molecules generally require cooler temperatures to form sufficiently stable hybrid complexes with the template. A primer need not reflect the exact sequence of the template but must be sufficiently complementary to hybridize with a template. The term "primer site" or "primer binding site" refers to the segment of the target nucleic acid to which a primer hybridizes.

A primer is said to anneal to another nucleic acid if the primer, or a portion thereof, hybridizes to a nucleotide sequence within the nucleic acid. The statement that a primer hybridizes to a particular nucleotide sequence is not intended to imply that the primer hybridizes either completely or exclusively to that nucleotide sequence. For example, in certain embodiments, amplification primers used herein are said to "anneal to a nucleotide tag". This description encompasses probe/primers that anneal wholly to the nucleotide tag, as well as probe/primers that anneal partially to the nucleotide tag and partially to an adjacent nucleotide sequence, e.g., a target nucleotide sequence. Such hybrid primers can increase the specificity of the amplification reaction.

As used herein, the selection of primers "so as to avoid substantial annealing to the target nucleic acids" means that primers are selected so that the majority of the amplicons detected after amplification are "full-length" in the sense that they result from priming at the expected sites at each end of the target nucleic acid, as opposed to amplicons resulting from priming within the target nucleic acid, which produces shorter-than-expected amplicons. In various embodiments, primers are selected so that at least 55%, at least 60%, at least 65%, at least 70%, at least 75%, at least 80%, at least 85%, at least 90%, at least 95%, at least 96%, at least 97%, at least 98%, or at least 99% of amplicons are full-length.

The term "primer pair" refers to a set of primers including a 5' "upstream primer" or "forward primer" that hybridizes with the complement of the 5' end of the DNA sequence to be amplified and a 3' "downstream primer" or "reverse primer" that hybridizes with the 3' end of the sequence to be amplified. As will be recognized by those of skill in the art, the terms "upstream" and "downstream" or "forward" and "reverse" are not intended to be limiting, but rather provide illustrative orientation in particular embodiments.

A "probe" is a nucleic acid capable of binding to a target nucleic acid of complementary sequence through one or more types of chemical bonds, generally through complementary base pairing, usually through hydrogen bond formation, thus forming a duplex structure. The probe binds or hybridizes to a "probe binding site." The probe can be labeled with a detectable label to permit facile detection of the probe, particularly once the probe has hybridized to its complementary target. Alternatively, however, the probe may be unlabeled, but may be detectable by specific binding with a ligand that is labeled, either directly or indirectly. Probes can vary significantly in size. Generally, probes are at least 7 to 15 nucleotides in length. Other probes are at least 20, 30, or 40 nucleotides long. Still other probes are somewhat longer, being at least 50, 60, 70, 80, or 90 nucleotides long. Yet other probes are longer still, and are at least 100, 150, 200 or more nucleotides long. Probes can also be of any length that is within any range bounded by any of the above values (e.g., 15-20 nucleotides in length).

A primer or probe sequence can be perfectly complementary to the sequence to which it hybridizes or can be less than perfectly complementary. In certain embodiments, the primer or probe sequence has at least 65% identity to the complement of the target nucleic acid sequence over a sequence of at least 7 nucleotides, more typically over a sequence in the range of 10-30 nucleotides, and often over a sequence of at least 14-25 nucleotides, and more often has at least 75% identity, at least 85% identity, at least 90% identity, or at least 95%, 96%, 97%. 98%, or 99% identity. It will be understood that certain bases (e.g., the 3' base of a primer) are generally desirably perfectly complementary to corresponding bases of the target nucleic acid sequence.

The terms "nucleotide tag sequence," "nucleotide tag" and "tag sequence" is used herein to refer to a predetermined nucleotide sequence that is added to a target nucleotide sequence. The nucleotide tag can encode an item of information about the target nucleotide sequence, such the identity of the target nucleotide sequence or the identity of the sample from which the target nucleotide sequence was derived. In certain embodiments, such information may be encoded in one or more nucleotide tags, e.g., a combination of two nucleotide tags, one on either end of a target nucleotide sequence, can encode the identity of the target nucleotide sequence.

As used herein, the term "encoding reaction" refers to reaction in which at least one nucleotide tag is added to a target nucleotide sequence. This process may be referred to as "tagging." Nucleotide tags can be added, for example, by an "encoding PCR" in which the at least one primer comprises a target-specific portion and a nucleotide tag located on the 5' end of the target-specific portion, and a second primer that comprises only a target-specific portion or a target-specific portion and a nucleotide tag located on the 5' end of the target-specific portion. For illustrative examples of PCR protocols applicable to encoding PCR, see, e.g., PCT Publication Nos. WO 2004/051218 and WO US03/37808, as well as U.S. Pat. No. 6,605,451, which are hereby incorporated by reference in their entirety. Nucleotide tags can also be added by an "encoding ligation" reaction that can comprise a ligation reaction in which at least one primer comprises a target-specific portion and nucleotide tag located on the 5' end of the target-specific portion, and a second primer that comprises a target-specific portion only or a target-specific portion and a nucleotide tag located on the 5' end of the target specific portion. Illustrative encoding ligation reactions are described, for example, in U.S. Pat. No. 7,601,821 and Patent Publication No. 2005/0260640, which is hereby incorporated by reference in its entirety, and in particular for ligation reactions. Nucleotide tags can also be added by other amplification methods; see below.

As used herein an "encoding reaction" produces a "tagged target nucleotide sequence" or "tagged target polynucleotide", which include a nucleotide tag linked to a target nucleotide sequence.

As used herein with reference to a portion of a primer, the term "target-specific" nucleotide sequence refers to a sequence that can specifically anneal to a target nucleic acid or a target nucleotide sequence under suitable annealing conditions.

As used herein with reference to a portion of a probe/primer, the term "nucleotide tag recognition sequence" refers to a sequence that can specifically anneal to a nucleotide tag under suitable annealing conditions.

"Amplification," according to the present teachings encompasses any means by which at least a part of at least one target nucleic acid is reproduced, typically in a template-dependent manner, including without limitation, a broad range of techniques for amplifying nucleic acid sequences, either linearly or exponentially. Illustrative means for performing an amplifying step include ligase chain reaction (LCR), ligase detection reaction (LDR), ligation followed by Q-replicase amplification, polymerase chain reaction (PCR), primer extension, strand displacement amplification (SDA), hyperbranched strand displacement amplification, multiple displacement amplification (MDA), nucleic acid strand-based amplification (NASBA), two-step multiplexed amplifications, rolling circle amplification (RCA), and the like, including multiplex versions and combinations thereof, for example but not limited to, OLA/PCR, PCR/OLA, LDR/PCR, PCR/PCR/LDR, PCR/LDR, LCR/PCR, PCR/LCR (also known as combined chain reaction—CCR), and the like. Descriptions of such techniques can be found in, among other sources, Ausbel et al.; PCR Primer: A Laboratory Manual, Diffenbach, Ed., Cold Spring Harbor Press (1995); The Electronic Protocol Book, Chang Bioscience (2002); Msuih et al., J. Clin. Micro. 34:501-07 (1996); The Nucleic Acid Protocols Handbook, R. Rapley, ed., Humana Press, Totowa, N.J. (2002); Abramson et al., Curr Opin Biotechnol. 1993 February; 4(1):41-7, U.S. Pat. Nos. 6,027,998; 6,605,451, Barany et al., PCT Publication No. WO 97/31256; Wenz et al., PCT Publication No. WO 01/92579; Day et al., Genomics, 29(1): 152-162 (1995), Ehrlich et al., Science 252:1643-50 (1991); Innis et al., PCR Protocols: A Guide to Methods and Applications, Academic Press (1990); Favis et al., Nature Biotechnology 18:561-64 (2000); and Rabenau et al., Infection 28:97-102 (2000); PHILLIP BELGRADER, MICHAEL M. MARINO, MATTHEW LUBIN, FRANCIS BARANY. Genome Science and Technology. 1(2): 77-87, (1996); Belgrader, Barany, and Lubin, Development of a Multiplex Ligation Detection Reaction DNA Typing Assay, Sixth International Symposium on Human Identification, 1995 (available on the world wide web at: promega.comigeneticidproc/ussymp6proc/blegrad.html-); LCR Kit Instruction Manual, Cat. #200520, Rev. #050002, Stratagene, 2002; Barany, Proc. Natl. Acad. Sci. USA 88:188-93 (1991); Bi and Sambrook, Nucl. Acids Res. 25:2924-2951 (1997); Zirvi et al., Nucl. Acid Res. 27:e40i-viii (1999); Dean et al., Proc Natl Acad Sci USA 99:5261-66 (2002); Barany and Gelfand, Gene 109:1-11 (1991); Walker et al., Nucl. Acid Res. 20:1691-96 (1992); Polstra et al., BMC Inf. Dis. 2:18-(2002); Lage et al., Genome Res. 2003 February; 13(2):294-307, and Landegren et al., Science 241:1077-80 (1988), Demidov, V., Expert Rev Mol. Diagn. 2002 November; 2(6):542-8., Cook et al., J Microbiol Methods. 2003 May; 53(2):165-74, Schweitzer et al., Curr Opin Biotechnol. 2001 February; 12(1):21-7, U.S. Pat. Nos. 5,830,711, 6,027,889, 5,686,243, PCT Publication No. WO0056927A3, and PCT Publication No. WO9803673A1. Each of the aforelisted references is incorportated herein by reference. In some embodiments, amplification comprises at least one cycle of the sequential procedures of: annealing at least one primer with complementary or substantially complementary sequences in at least one target nucleic acid; synthesizing at least one strand of nucleotides in a template-dependent manner using a polymerase; and denaturing the newly-formed nucleic acid duplex to separate the strands. The cycle may or may not be repeated. Amplification can comprise thermal cycling or can be performed isothermally.

"Polymerase Chain Reaction Amplification," or "PCR" refers to an amplification method in which thermal cycling, consisting of cycles of repeated heating and cooling of the reaction for DNA melting and enzymatic replication of the DNA. PCR Thermal cycling protocols are well known in the art. Typically, PCR consists of a series of 20-40 cycles. For example, and not limitation the cycle may include a denaturation step, an annealing step (allowing annealing of the primers to the single-stranded DNA template) and an extension/elongation step. Each step may occur at a particular temperature, for a particular length of time, and under particular reaction conditions. For example, and not for limitation, the temperature of the denaturation step may be 95° C., the temperature of the annealing step (Ta) may be 62° C., and the temperature of the extension/elongation step may be 72° C. In some PCR protocols (e.g., touchdown PCR) a high annealing temperature in initial cycles may be descreased in increments ininitial cycles. For purposes of the invention, in such protocols, the Ta is defined as the annealing temperature used in the majority of the cycles.

The term "qPCR" is used herein to refer to quantitative real-time polymerase chain reaction (PCR), which is also known as "real-time PCR" or "kinetic polymerase chain reaction."

A "reagent" refers broadly to any agent used in a reaction, other than the analyte (e.g., nucleic acid being analyzed). Illustrative reagents for a nucleic acid amplification reaction include, but are not limited to, buffer, metal ions, polymerase, reverse transcriptase, primers, template nucleic acid, nucleotides, labels, dyes, nucleases, and the like. Reagents for enzyme reactions include, for example, substrates, cofactors, buffer, metal ions, inhibitors, and activators.

The term "label," as used herein, refers to any atom or molecule that can be used to provide a detectable and/or quantifiable signal. In particular, the label can be attached, directly or indirectly, to a nucleic acid or protein. Suitable labels that can be attached to probes include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates.

The term "dye," has its standard meaning in the art. The term "fluorescent dye," as used herein, generally refers to any dye that emits electromagnetic radiation of longer wavelength by a fluorescent mechanism upon irradiation by a source of electromagnetic radiation, such as a lamp, a photodiode, or a laser.

The term "reporter molecule" refers to a molecule capable of generating a fluorescence signal. A "quencher molecule" refers to a molecule capable of absorbing the fluorescence energy of an excited reporter molecule, thereby quenching the fluorescence signal that would otherwise be released from the excited reporter molecule. In order for a quencher molecule to quench an excited fluorophore, it is often advantageous that the quencher molecule is within a minimum quenching distance of the excited reporter molecule at some time starting from the excitation of the reporter molecule, but prior to the reporter molecule releasing the stored fluorescence energy. In proximity based quenching applications, the reporter and quencher molecules are positioned sufficiently close to each other such that whenever the reporter molecule is excited, the energy of the excited state transfers to the quencher molecule where it either dissipates nonradiatively or is emitted at a different emission frequency than that of the reporter molecule. Several non-radiative energy transfer mechanisms work over shorter distances and are appropriate for proximity based quenching applications.

The term "elastomer" has the general meaning used in the art. Thus, for example, Allcock et al. (Contemporary Polymer Chemistry, 2nd Ed.) describes elastomers in general as polymers existing at a temperature between their glass transition temperature and liquefaction temperature. Elastomeric materials exhibit elastic properties because the polymer chains readily undergo torsional motion to permit uncoiling of the backbone chains in response to a force, with the backbone chains recoiling to assume the prior shape in the absence of the force. In general, elastomers deform when force is applied, but then return to their original shape when the force is removed.

A "polymorphic marker" or "polymorphic site" is a locus at which a nucleotide sequence divergence occurs. Illustrative markers have at least two alleles, each typically occurring at a frequency of greater than 1%, and more typically greater than 10% or 20% of a selected population. A polymorphic site may be as small as one base pair. Polymorphic markers include restriction fragment length polymorphism (RFLPs), variable number of tandem repeats (VNTR's), hypervariable regions, minisatellites, dinucleotide repeats, trinucleotide repeats, tetranucleotide repeats, simple sequence repeats, deletions, and insertion elements such as Alu. The first identified allelic form is arbitrarily designated as the reference form and other allelic forms are designated as alternative or variant alleles. The allelic form occurring most frequently in a selected population is sometimes referred to as the wildtype form. Diploid organisms may be homozygous or heterozygous for allelic forms. A diallelic polymorphism has two forms. A triallelic polymorphism has three forms.

A "single nucleotide polymorphism" (SNP) occurs at a polymorphic site occupied by a single nucleotide, which is the site of variation between allelic sequences. The site is usually preceded by and followed by highly conserved sequences of the allele (e.g., sequences that vary in less than 1/100 or 1/1000 members of the populations). A SNP usually arises due to substitution of one nucleotide for another at the polymorphic site. A transition is the replacement of one purine by another purine or one pyrimidine by another pyrimidine. A transversion is the replacement of a purine by a pyrimidine or vice versa. SNPs can also arise from a deletion of a nucleotide or an insertion of a nucleotide relative to a reference allele.

B. Description

In one aspect, the invention provides a method for detecting a target nucleotide sequence comprising: a) tagging the target nucleotide sequence with a nucleotide tag sequence, thereby producing a tagged target nucleic acid sequence; b) providing a probe oligonucleotide comprising a nucleotide tag recognition sequence complementary to the nucleotide tag sequence and a regulatory sequence 5' to the nucleotide tag recognition sequence, wherein said probe oligonucleotide comprises a first label and has a melting temperature $Tm1$; c) amplifying the tagged target nucleic acid sequence in a PCR amplification reaction using the probe oligonucleotide as a primer, wherein said PCR amplification reaction is characterized by an annealing temperature $Ta$; wherein the PCR amplification reaction is carried out in the presence of a regulatory oligonucleotide comprising a sequence segment that is complementary to the regulatory sequence, wherein said regulatory oligonucleotide comprises a second label and has a melting temperature $Tm2$; and d) detecting the product of the PCR amplification reaction; wherein the first label and the second label constitute a fluorescent reporter/quencher pair; and wherein $Tm1$ and $Tm2$ are both higher than $Ta$. Without intending to be bound by a particular mechanism, carrying out a reaction in which both the Tm of the probe oligonucleotide and the Tm regulatory oligonucleotide are above Ta, reduces background signal (fluorescence) and provides a superior assay result.

In one aspect, the invention provides a method for detecting a polynucleotide with a target nucleotide sequence by tagging the polynucleotide comprising a desired target nucleotide sequence with a nucleotide tag, providing a probe oligonucleotide with a melting temperature $Tm1$, comprising a regulatory sequence and a nucleotide tag recognition sequence; incorporating the probe oligonucleotide into the tagged polynucleotide in a polynucleotide amplification reaction, providing a regulatory oligonucleotide with a melting temperature $Tm2$, comprising a sequence segment that is at least partially complementary to the regulatory sequence; wherein $Tm1$ and $Tm2$ are higher than the annealing temperature associated with the polynucleotide amplification reaction.

Tagging

In this method, a nucleotide tag sequence ("tag sequence" or "NTS") is associated with the target nucleotide sequence (TNS), in a process referred to as "tagging." In one embodiment, without limitation, the tag sequence is associated with the target nucleotide sequence in an amplification reaction. For example, the TNS can be amplified using the polymerase chain reaction (PCR) in which a first (e.g., "forward") primer includes the nucleotide tag sequence 5' to a target specific portion, resulting in an amplicon containing both the tag sequence and the TNS (e.g., the tag sequence 5' and adjacent to the TNS). In some embodiments, the amplification reaction uses a second (e.g., "reverse") primer.

In specific embodiments, the invention provides an amplification method for introducing each tag nucleotide sequence into one or more target nucleic acid(s). The method entails amplifying the one or more nucleic acid(s), typically in a plurality of samples. The samples can differ from one another in any way, e.g. the different samples can be from different tissues, subjects, environmental sources, etc. The tag sequence can be introduced as part of a tagging oligonucleotide. In an amplification reaction, e.g. PCR, the tagging oligonucleotide can function as a tagging primer, including a target nucleotide recognition sequence and a nucleotide tag. The recognition can be encoded by partial or complete complementarity between the target nucleotide sequence and the target nucleotide recognition sequence. Further, the nucleotide tags can be chosen in association with the target nucleotide recognition sequence(s) and can encode the target nucleotide sequence(s) in the target nucleic acid(s). A reverse primer flanking the sequence of interest can be provided.

The tag sequence can be incorporated immediately adjacent to the target specific sequence or with limited number of linker nucleotides in between. The number of linker nucleotides are preferably less than 25, more preferably less than 10, still more preferably less than 5. In particular embodiments, the probe oligonucleotide can be rescued from the regulatory oligonucleotide by hybridization to the tagged nucleic acid target(s). The hybridization can be directed to the nucleotide tag on the tagged target nucleic acid(s) that is recognized by a nucleotide tag recognition sequence on the probe oligonucleotide.

According to the present invention, the tag sequence and the TNS define a composite sequence stretch (CSS), which is more generally referred to as the "tagged target nucleic acid sequence", and sometimes referred to as "tagged polynucleotide target". Amplicons comprising the tagged target nucleic acid sequence can be double or single stranded.

Tagging primers, containing a target nucleotide recognition sequence and a tag sequence, are used to associate the nucleotide tag sequence into the "tagged target nucleic acid sequence. Preferably, the tagging primer is in the range of 15-60 nucleotides in length. More preferably, the tagging primer is in the range of 18-45 nucleotides in length. The precise sequence and length of the tagging primer depends in part on the nature of the target nucleotide sequence to which it binds. The sequence and length may be varied to achieve appropriate annealing and melting properties for a particular embodiment. Preferably, the tagging primer has a melting temperature, Tm in the range of 50-85° C. More preferably, the tagging primer has a melting temperature, Tm in the range of 60-75° C. In particular examples, the sequence and the length of the target nucleotide recognition sequence may be varied to achieve appropriate annealing and melting properties with the probe.

In embodiments in which the amplicon product of the amplification reaction is double stranded, the first strand will contain the tag sequence and the TNS, and the complementary strand will contain the complement of the sequences in the first strand. For purposes of clarity, the discussion below refers to the tag sequence and TNS, but it will be appreciated that equivalent assays may be carried out using the complementary sequences. One of skill guided by this disclosure will immediately recognize how to conduct the assays of the invention by detecting either strand, with appropriate adjustments to primer and probe sequences.

It will be appreciated that, depending on the nature of the step in which the tag sequence is associated with the target nucleotide sequence, the tagged target nucleic acid sequence can include additional sequence elements, for example if a forward primer includes sequences in addition to the tag sequence and the target specific portion and/or a reverse primer includes sequences in addition to target specific sequences.

Probe Oligonucleotide

The invention further relates to a probe oligonucleotide (sometimes referred to as "oligonucleotide probe") that associates with a portion of the tagged target nucleic acid sequence (CSS). That is, the probe oligonucleotide comprises a "nucleotide tag recognition sequence" portion complementary to the nucleotide tag sequence portion of the tagged target nucleic acid sequence, such that the oligonucleotide probe can hybridize to the tagged target nucleic acid sequence and act as a primer in an amplification reaction. The nucleotide tag recognition sequence can be partially or completely identical to the nucleotide tag sequence or its complement. The probe oligonucleotide generally also contains a regulatory sequence, usually 5' to the nucleotide tag sequence, as discussed below.

In one embodiment, the nucleotide tag recognition sequence of the probe oligonucleotide hybridizes to the complement of the nucleotide tag sequence. That is, the nucleotide tag sequence may be at the 5' end of one strand of the tagged target nucleic acid sequence (or "tagged polynucleotide"), and the probe oligonucleotide may hybridize to the complement of the nucleotide tag sequence, at the 3' end of the second strand of the tagged polynucleotide.

Preferably, the probe oligonucleotide is in the range of 15-60 nucleotides in length. More preferably, the probe oligonucleotide is in the range of 18-45 nucleotides in length. The precise sequence and length of an probe oligonucleotide depends in part on the nature of the nucleotide tag to which it binds. The overall sequence and length may be varied to achieve appropriate annealing and melting properties for a particular embodiment. The melting temperature of the probe oligonucleotide may be greater than 95° C. The melting temperature of the probe oligonucleotide can fall within a range of, 50-85° C., 55-80° C., 60-75° C., 65-70° C., 75° C., 60-120° C., 75-115° C. or more or it can fall within a range having one of these values as endpoints (e.g. 50-75° C.). Preferably, the probe oligonucleotide has a melting temperature, Tm in the range of 55-85° C. More preferably, the probe oligonucleotide has a melting temperature, Tm in the range of 65-75° C., ever more preferably >75° C. In some embodiments the calculated Tm for the probe oligonucleotide may be >100° C. In particular examples, the nucleotide tag recognition sequence and length may be varied to achieve appropriate annealing and melting properties in the initial cycles of an amplification reaction when the probe is first incorporated into the polynucleotide.

Amplification of the Tagged Target Nucleic Acid Sequence by the Probe Oligonucleotide In some embodiments the tagged target nucleic acid sequence (or a portion thereof) is amplified in a PCR amplification reaction using the probe oligonucleotide as a primer. Generally the amplification reaction includes a 3' (reverse) primer. It will be recognized that, when the probe oligonucleotide comprises a regulatory sequence, the product of the amplification will include the regulatory sequence, the nucleotide tag sequence, and the target nucleotide sequence.

The probe oligonucleotide can be further incorporated into longer nucleic acid constructs in a tagged target nucleic acid dependent method. For example, the probe oligonucleotide can be ligated to another nucleic acid facilitated by proximity via hybridization to the tagged target nucleic acid(s). More often, the probe oligonucleotide can serve as a primer in an amplification reaction where it is incorporated to the tagged target nucleic acid(s).

The PCR amplification reaction is characterized by an annealing temperature Ta (see below). According to the present invention, the melting temperature of the probe oligonucleotide (Tm1) is greater than the Ta of the amplification reaction. In some embodiments Tm1 is at least 1° C., at least 2° C., at least 3° C., at least 4° C., at least 5° C., at least 6° C., at least 7° C., at least 8° C., at least 9° C., at least 10° C., at least 11° C., at least 12° C., at least 13° C., at least 14° C., at least 15° C., at least 16° C., at least 17° C., at least 18° C., at least 19° C., at least 20° C., at least 21° C., at least 22° C., at least 23° C., at least 24, at least 25° C., at least 35° C. or at least 50° C. higher than the annealing temperature. In some embodiments, Tm1 is at least 50° C. higher than the annealing temperature (Ta). In some embodiments Tm1 is at least 25° C. higher than Tm2.

The PCR amplification reaction is carried out in the presence of a regulatory oligonucleotide, as discussed below.

Regulatory Oligonucleotide

The invention relates to a regulatory oligonucleotide, which comprises a sequence segment complementary to the regulatory sequence of the probe oligonucleotide. Annealing of the sequence segment of the regulatory oligonucleotide to the regulatory sequence of the probe oligonucleotide competes with the association of the probe oligonucleotide and the tagged target nucleic acid sequence (or "CSS") during the amplification reaction.

Preferably, the regulatory oligonucleotide is in the range of 6-60 nucleotides in length. More preferably, the regulatory oligonucleotide is in the range of 15-45 nucleotides in length. Even more preferably, the regulatory oligonucleotide is in the range of 18-30 nucleotides in length. In some embodiments the regulatory oligonucleotide may comprise nucleotides that flank the sequence segment (e.g., 1, 2, 3, 4, 5, 6, 7, 8, 9, 10 or more than 10 nucleotides). See Example 2. In some embodiments, sequence segment comprises all or most (e.g., at least 80% or at least 90%) of the length of the regulatory oligonucleotide. In some embodiments, sequence segment is in the range of 6-60 nucleotides in length, more preferably, in the range of 15-45 nucleotides in length, and even more preferably in the range of 18-30 nucleotides in length. The precise sequence and length of the regulatory oligonucleotide depends in part on the nature of the probe oligonucleotide to which it binds. The sequence and length may be varied to achieve appropriate annealing and melting properties for a particular embodiment.

The melting temperature of the regulatory oligonucleotide (Tm2) can fall within a range of, 45-85° C., 50-80° C., 55-75° C., 60-70° C., 65-75° C. or it can fall within a range having one of these values as endpoints (e.g. 50-75° C.). Preferably, the regulatory oligonucleotide has a melting temperature, Tm in the range of 50-85° C. More preferably, the regulatory oligonucleotide has a melting temperature, Tm in the range of 60-75° C. In particular examples, the sequence and the length of the segment recognizing the regulatory sequence may be varied to achieve appropriate annealing and melting properties with the probe. In some embodiments, a competitive auxiliary sequence may be added to increase the specificity of the probe oligonucleotide for the tagged target nucleic acid.

According to the present invention, the melting temperature of the regulatory oligonucleotide (Tm2) is greater than the Ta of the amplification reaction. In some embodiments Tm2 is at least 1° C., at least 2° C., at least 3° C., at least 4° C., at least 5° C., at least 6° C., at least 7° C., at least 8° C., at least 9° C., at least 10° C., at least 11° C., at least 12° C., at least 13° C., at least 14° C., at least 15° C., at least 16° C., at least 17° C., at least 18° C., at least 19° C., at least 20° C., at least 21° C., at least 22° C., at least 23° C., at least 24 or at least 25° C. higher than the annealing temperature.

Preferably, the 3' terminal nucleotide of the regulatory oligonucleotide is blocked or rendered incapable of extension by a nucleic acid polymerase. Such blocking is conveniently carried out by the attachment of a reporter or quencher molecule to the terminal 3' carbon of the probe oligonucleotide by a linking moiety.

Typically, the probe oligonucleotide will have a sequence that is complementary to the targeted tagged polynucleotide(s), which is far longer than the regulatory sequence, said regulatory oligonucleotide being complementary to said regulatory sequence. As such, the regulatory oligonucleotide competes against the targeted tagged polynucleotide(s) to hybridize with the probe oligonucleotide, but will typically be at a disadvantage from the complementarity aspect. However, the regulatory oligonucleotide will have a higher success competing against the untargeted nucleic acids, to which the probe oligonucleotide may bind nonspecifically, from the complementarity aspect and may therefore reduce nonspecific incorporation of the probe in the reaction. In addition, the regulatory oligonucleotide can be supplied at higher concentrations, further increasing its competition against the untargeted nucleic acid(s).

In various embodiments, the concentration of the regulatory oligonucleotide can be in excess of the probe oligonucleotide. In some embodiments, the concentration of the regulatory oligonucleotide can be adjusted according to the total nucleic acid(s) in the reaction. The regulatory oligonucleotide can be supplied in excess of at least 10%, 50%, 100%, 500%, 1000% or more over the oligonucletide probe or the total nucleic acid(s) in the reaction.

Auxiliary Sequence

The regulatory oligonucleotide can have an auxiliary sequence that acts as a competitive sequence against the target nucleic acid/probe oligonucleotide hybridization. When the probe oligonucleotide and the regulatory oligonucleotide are aligned along the regulatory sequence, the auxiliary sequence segment can at least partially overlap with the probe oligonucleotide, more typically with the nucleotide tag recognition sequence. That is, the regulatory oligonucleotide can comprise a sequence complementary to both the regulatory sequence and at least a portion of the nucleotide tag recognition sequence of the probe oligonucleotide. Put differently, the sequence segment of the regluatory oligonucleotide can be complementary to the regulatory sequence and at least a portion of the nucleotide tag recognition sequence of the probe oligonucleotide. The degree of complementarity between the auxiliary sequence and the probe oligonucleotide can be adjusted to regulate specificity. In embodiments, wherein the probe oligonucleotide is incorporated into the tagged polynucleotide in an amplification reaction, the auxiliary sequence can compete against non-specific sites, more specifically untagged nucleic acid(s) even in the initial cycles of an amplification reaction. The hybridization of the regulatory oligonucleotide and the probe oligonucleotide along the regulatory sequence can enhance the hybridization of the auxiliary sequence to the probe oligonucleotide, since the auxiliary sequence would be presented at increased local concentrations compared to free nucleic acid(s). In addition, the concentration of the regulatory oligonucleotide, and thus the auxiliary sequence, can be adjusted to allow it to compete effectively against untagged nucleic acid(s). In specific embodiments, the regulatory oligonucleotide can be provided at 1.5 to 4-fold excess, 1 to 10-fold excess, 4 to 10-fold excess, 1.5 to 50-fold excess, 4 to 50, 100-fold excess or any other range having any of these values as endpoints (e.g., 1.5 to 10-fold excess). With these advantages, the auxiliary sequence can regulate specificity at even low to zero complementarity for the probe oligonucleotide. At low to no complementarity between the auxiliary sequence and the probe oligonucleotide, the probe oligonucleotide hybridization to the tagged nucleic acid(s) would successfully outcompete the auxiliary sequence on the regulatory oligonucleotide.

Further, a quencher sequence can be incorporated into the regulatory oligonucleotide sequence to increase quenching. In preferred embodiments one or more deoxyguanosine nucleotides will be incorporated to the quencher sequence around the hybridization site of the reporter molecule on the probe oligonucleotide. In some embodiments, a deoxyguanosine tail can be added to the quencher sequence, 3' to the regulatory sequence hybridization.

Correspondence of Signal and the Presence of the Target Sequence

Association with the regulatory oligonucleotide affects the signal associated with the probe oligonucleotide. Accordingly, the interaction of the probe oligonucleotide with the CSS prevents the probe oligonucleotide from hybridizing to the regulatory oligonucleotide. As a result, a change in probe oligonucleotide-associated signal aids in the detection of a target nucleotide sequence.

The incorporation of the tag sequence is designed to be dependent on the presence of the specific TNS. As a result, the present invention links the presence of a specific nucleotide sequence (i.e., a specific target nucleic acid sequence) in a sample to a change in signal. The signal can be acquired before and after the sample is interrogated with the detection method of the present invention. Accordingly, a change in signal is interpreted to be associated with the presence of a specific TNS. Further, the present invention also relates to monitoring the amplification of a target polynucleotide sequence. Accordingly, the present invention relates to a method for monitoring nucleic acid amplification of a target sequence by following the change in signal over time.

In various embodiments of the invention, the changed signal associated with the incorporation of the probe oligonucleotide to a tagged nucleotide relates to the release of the probe oligonucleotide from a regulatory oligonucleotide. The association of the regulatory oligonucleotide to unincorporated probe oligonucleotide forms a reporter/quencher pair such that a possible signal is quenched under conditions suitable for this association. The incorporation of the probe oligonucleotide to a tagged target nucleic acid disrupts the formation of such a reporter/quencher pair resulting in a change in signal. In various embodiments, the probe oligonucleotide is labeled with the reporter molecule and the regulatory oligonucleotide is labeled with a quencher molecule. Exemplary reporter/quencher pairs comprise fluorescence dyes and their quenchers.

In some embodiments, a plurality of probe oligonucleotides will be specifically directed to different tag sequences. The signal associated with each tag sequence is differentiated by linking each probe oligonucleotide recognizing a particular nucleotide tag to a specific reporter or quencher.

In the present assay approach, when a complementary target sequence is present, hybridization of the probe to the complementary target sequence disrupts the hybridization of the regulatory oligonucleotide to the probe, wherein the quencher molecule is no longer close enough to the reporter molecule to quench the reporter molecule. As a result, the probes provide an increased fluorescent signal when hybridized to a target sequence than when unhybridized.

Annealing Temperature

During the annealing phase of a polynucleotide amplification reaction, the primers anneal to polynucleotides to prime an elongation reaction at the elongation temperature. The "annealing temperature" of an amplification reaction is usually determined experimentally to obtain highest yields with desired specificities. Generally, higher annealing temperatures increase specificity for the targeted polynucleotide. The fraction of annealed primers at a target site in a reaction directly affects overall yield and depends on many factors, including competing sites in the target and other polynucleotides in the reaction, the annealing time, the melting temperature associated with the complementary region of the primer with the target site and the annealing temperature. Higher annealing temperatures affect primer binding energies to non-specific competing sites in the reaction and thus may shift this population of primer to specific target sites. Higher annealing temperatures also increase the fraction of single stranded target polynucleotides in the reaction that are available for primer binding. However, higher annealing temperatures have a disabling effect on specific primer binding to target sites by affecting the binding free energy for this interaction. Desired annealing temperatures assist the reaction yield by increasing the fraction of annealed primers to the targeted site.

A "yielding annealing temperature" falls in a temperature range that results in the amplification of desired targets at a rate higher than the amplification of untargeted polynucleotide sequences in the reaction. A yielding annealing temperature for each amplification reaction can be independently chosen. Yielding annealing temperatures can be chosen from a range of temperatures, for example the annealing temperature can within a range of 15° C.-80° C., 30° C.-75° C., 40° C.-75° C., 50° C.-72° C., 60° C.-64° C., 55° C.-62°, 63° C., 64° C., 65° C. or can fall within any range having one of these temperatures as endpoints (e.g. 50° C.-62° C.). In some embodiments, the amplification reaction is PCR.

The hybridization specificity of an oligonucleotide to a target site is increased by decreasing oligonucleotide binding to non-specific sites. Non-specific target sites are usually sites with lower complementarity, but for the purpose of the reaction, they are generally sites where oligonucleotide binding is not desired.

There are several techniques addressing the increased specificity requirements at a given annealing temperature. These techniques allow the use of lower annealing temperatures and employ competitive inhibitors for the binding of a primer and a target nucleic acid. Puskas et al., Genome Research 5:309-311 (1995) and Harry et al., BioTechniques, 24:445-450 (1998), which are hereby incorporated by reference, provide primers that are complementary to a target nucleotide sequence and oligonucleotides that are partially complementary to said target nucleotide sequence and are 3' modified to prevent elongation. These oligonucleotides increase specificity by occupying non-specific sites that the primers would have annealed to and divert the primer population towards the target nucleotide sequence instead. Due to their partial complementarity to the target nucleotide sequence, the primers are able to compete successfully against the partially complementary oligonucleotides for the target nucleotide sequences. Kong et al., Biotechnology Letters, 26:277-280 (2004), which is hereby incorporated by reference, employs as competitive inhibitors, oligonucleotides that are partially complementary to the primers. These oligonucleotides compete successfully against non-specific sites for the primers and increase specificity by making the primers less available for said sites. Due to their reduced complementarity, the target nucleotide sequences can outcompete said oligonucleotides for primer binding.

The various oligonucleotides can be selected to achieve a desired degree of specificity at the chosen annealing temperatures. The target nucleotide recognition sequence on the tagging primer(s) can specifically anneal to a target nucleotide sequence under suitable conditions and at the chosen annealing temperature. The conditions can be selected such that the primer annealing will be sensitive to variations in the target nucleotide sequence. Generally, nucleotide mismatches towards the 3' end of a primer greatly affect elongation from a primer. To differentiate between sequence variants, the primer can be designed such that the 3' end of it would be directed to the polymorphic site. Alternatively, sequences with higher melting temperatures can be chosen achieving less specific annealing to a broader variety of target nucleotide sequences.

With high specificity sequences, the primer can effectively differentiate between polymorphisms in the target nucleic acid(s). The polymorphisms can encompass single or multiple nucleotide changes at one or more polymorphic site(s). The changes at the polymorphic site(s) can involve deletions, insertions and substitutions of single all multiple nucleotides. Elongation from the primer is particularly sensitive to the hybridization stability at the 3' end of the primer. Primers designed to align with a polymorphic site at their 3' end are thus especially useful to differentiate between various alleles.

Tagging and Detection Reactions

The target nucleotide tagging and detection can be conducted in separate reactions. Alternatively, these two steps can be performed in a common reaction volume. A double amplification method can be used to incorporate a tagging primer comprising a target nucleotide recognition sequence and a nucleotide tag and an oligonucleotide primer/probe comprising a nucleotide tag recognition sequence, a regulatory sequence and a signal moiety.

Reporter and Quencher Pairs

In various embodiments, the invention provides one or more pairs of a probe oligonucleotide and a regulatory oligonucleotide that specifically anneal to each other, wherein one of them is labeled with a reporter molecule and the other with a quencher molecule of a reporter-quencher pair. When the probe oligonucleotide and the regulatory oligonucleotide are aligned along the regulatory sequence, the reporter molecule and quencher molecule are positioned on the oligonucleotides sufficiently close to each other such that whenever the reporter molecule is excited, the energy of the excited state nonradiatively transfers to the quencher molecule where it either dissipates nonradiatively or is emitted at a different emission frequency than that of the reporter molecule. Typically, the probe oligonucleotide will comprise the reporter molecule and the regulatory oligonucleotide will comprise the quencher molecule, however this positioning can be reversed and this modifications will be apparent to practitioners skilled in this art.

In some embodiments the assay of the invention uses an probe oligonucleotide containing a reporter molecule and a regulatory oligonucleotide containing a quencher molecule, said reporter and quencher molecules being members of a reporter-quencher pair. The regulatory oligonucleotide comprises a sequence that hybridizes to a regulatory sequence in the probe oligonucleotide. The probe oligonucleotide specifically anneals to a region of a target tagged polynucleotide with a target nucleotide sequence, such that the nucleotide tag recognition sequence hybridizes to a nucleotide tag in the tagged polynucleotide. The nucleotide tag is typically incorporated to the target polynucleotide using a tagging primer comprising a nucleotide tag sequence and a target nucleotide recognition sequence, where the target nucleotide recognition sequence hybridizes to the target nucleotide sequence. An amplification reaction, typically PCR, is carried out to incorporate the tagging primer into the target polynucleotide (i.e., producing amplicons containing both the nucleotide tag sequence and the target nucleotide sequence).

When the regulatory oligonucleotide hybridizes to the probe oligonucleotide along the regulatory sequence, the reporter molecule and quencher molecule are positioned sufficiently close to each other such that whenever the reporter molecule is excited, the energy of the excited state nonradiatively transfers to the quencher molecule where it either dissipates nonradiatively or is emitted at a different emission frequency than that of the reporter molecule. During strand extension by a DNA polymerase, the probe oligonucleotide anneals to the template and acts as a primer. As a result of the probe is incorporated into an amplicon and the reporter molecule is effectively separated from the quencher molecule such that the quencher molecule is no longer close enough to the reporter molecule to quench the reporter molecule's fluorescence. Thus, as more and more probe oligonucleotides are incorporated into double-stranded polynucleotides during amplification, larger numbers of reporter molecules are released from close proximity interactions with quencher molecules, thus resulting in an increasing number of unquenched reporter molecules which produce a stronger and stronger fluorescent signal. The detection is typically carried out under conditions wherein higher than a desired fraction of unincorporated probe oligonucleotide is hybridized to the regulatory oligonucleotide. During any stage of the detection, the amount of the unincorporated probe oligonucleotide that is hybridized to the regulatory oligonucleotide is preferably greater than 50%, 80%, 90%, 95%, 99%, 99.5%, 99.9%, 99.95% or more of the total unincorporated probe oligonucleotide. The detection conditions are also selected such that the amount of unincorporated probe oligonucleotide that is not associated to the regulatory oligonucleotide is low compared to the incorporated probe oligonucleotide. During any stage of the detection, the amount of unincorporated oligonucleotide that is not associated to the regulatory oligonucleotide is preferably less than 50%, 20%, 10%, 5%, 1%, 0.5%, 0.1%, 0.05% or less of the incorporated probe oligonucleotide.

In various embodiments, the invention provides a detection method for one or more target nucleic acid(s), typically one or more target polynucleotide(s), using one or more probe oligonucleotide(s). The probe oligonucleotide's signal can be modulated by rescuing the probe from a regulatory oligonucleotide recognizing a regulatory sequence on the probe. The recognition can be encoded in a sequence segment in the regulatory oligonucleotide with partial or complete complementarity to the regulatory sequence on the probe oligonucleotide.

Various factors influence the utility of reporter-quencher molecule pairs in hybridization and amplification assays. The first factor is the effectiveness of the quencher molecule to quench the reporter molecule. This first factor, herein designated "$RQ^-$", can be characterized by the ratio of the fluorescent emissions of the reporter molecule to the quencher molecule when the probe is not hybridized to a perfectly complementary polynucleotide. That is, $RQ^-$ is the ratio of the fluorescent emissions of the reporter molecule to the energy that is transferred to the quencher molecule when the probe oligonucleotide is hybridized to the regulatory oligonucleotide. Influences on the value of $RQ^-$ include, for example, the particular reporter and quencher molecules used, the spacing between the reporter and quencher molecules in the hybridized complex, nucleotide sequence-specific effects, and the degree of flexibility of structures, and the presence of impurities. A related quantity $RQ^+$, refers to the ratio of fluorescent emissions of the reporter molecule to the energy that is transferred to quencher molecule when the probe oligonucleotide is hybridized to a complementary polynucleotide.

A second factor is the efficiency of the probe to hybridize to a complementary polynucleotide. This second factor depends on the probe's melting temperature, $T_m$, the presence of a secondary structure in the probe or target polynucleotide, the temperature of the reaction, and other reaction conditions.

A third factor is the efficiency of the regulatory oligonucleotide to hybridize to the probe oligonucleotide.

This third factor depends on the regulatory oligonucleotide's melting temperature, $T_m$, the degree of complementarity between the regulatory oligonucleotide and the probe oligonucleotide, the presence of a secondary structure in the probe or regulatory oligonucleotide, the temperature of the reaction, and other reaction conditions.

A fourth factor is the oligonucleotide sequence in the vicinity of the reporter molecule. Depending on the sequence, the fluorescence intensity of the probe is either increased or decreased by hybridization. A strong degree of quenching is observed by hybridization to sequences containing deoxyguanosine nucleotides (Gs), giving a sequence specific decrease in flurescence. For additional discussion of this effect, see Crocket et al., Analytical Biochemistry, 290:89-97 (2001) and Behlke et al., Fluorescence Quenching by Proximal G-bases (available on the world wide web at: http: double backslash cdn.idtdna.com/Support/Technical/TechnicalBulletinPDF/Fluorescence_quenching_by_proxi mal_G_bases.pdf).

Preferably, reporter molecules are fluorescent organic dyes derivatized for attachment to the terminal 3' carbon or terminal 5' carbon of the probe oligonucleotide and the regulatory oligonucleotide via a linking moiety. Preferably, quencher molecules are also organic dyes, which may or may not be fluorescent, depending on the embodiment of the invention. For example, in a preferred embodiment of the invention, the quencher molecule is fluorescent. Generally whether the quencher molecule is fluorescent or simply releases the transferred energy from the reporter by non-radiative decay, the absorption band of the quencher should substantially overlap the fluorescent emission band of the reporter molecule. Non-fluorescent quencher molecules (NFQMs), such as Black Hole quenchers, that absorb energy from excited reporter molecules, but which do not release the energy radiatively, are known in the art and may be used.

There is a great deal of practical guidance available in the literature for selecting appropriate reporter-quencher pairs for particular probes, as exemplified by the following references: Clegg (cited above); Wu et al. (cited above); Pesce et al., editors, Fluorescence Spectroscopy (Marcel Dekker, New York, 1971); White et al., Fluorescence Analysis: A Practical Approach (Marcel Dekker, New York, 1970); and the like. The literature also includes references providing exhaustive lists of fluorescent molecules and NFQMs, and their relevant optical properties for choosing reporter-quencher pairs, e.g., Berlman, Handbook of Fluorescence Spectra of Aromatic Molecules, 2nd Edition (Academic Press, New York, 1971); Griffiths, Colour and Constitution of Organic Molecules (Academic Press, New York, 1976); Bishop, editor, Indicators (Pergamon Press, Oxford, 1972); Haugland, Handbook of Fluorescent Probes and Research Chemicals (Molecular Probes, Eugene, 1992) Pringsheim, Fluorescence and Phosphorescence (Interscience Publishers, New York, 1949); and the like. Further, there is extensive guidance in the literature for derivatizing reporter and quencher molecules for covalent attachment via common reactive groups that can be added to an oligonucleotide, as exemplified by the following references: Haugland (cited above); Ullman et al., U.S. Pat. No. 3,996,345; Khanna et al., U.S. Pat. No. 4,351,760; and the like.

Exemplary reporter-quencher pairs may be selected from xanthene dyes, including fluoresceins, and rhodamine dyes. Many suitable forms of these compounds are widely available commercially with substituents on their phenyl moieties which can be used as the site for bonding or as the bonding functionality for attachment to an oligonucleotide. Another group of fluorescent compounds are the naphthylamines, having an amino group in the alpha or beta position. Included among such naphthylamino compounds are 1-dimethylaminonaphthyl-5-sulfonate, 1-anilino-8-naphthalene sulfonate and 2-p-touidinyl-6-naphthalene sulfonate. Other dyes include 3-phenyl-7-isocyanatocoumarin, acridines, such as 9-isothiocyanatoacridine and acridine orange; N-(p-(2-benzoxazolyl)phenyl)maleimide; benzoxadiazoles, stilbenes, pyrenes, and the like.

Preferably, reporter and quencher molecules are selected from fluorescein and rhodamine dyes. These dyes and appropriate linking methodologies for attachment to oligonucleotides are described in many references, e.g., Khanna et al. (cited above); Marshall, Histochemical J., 7:299-303 (1975); Menchen et al., U.S. Pat. No. 5,188,934; Menchen et al., European Patent Application 87310256.0; and Bergot et al., International Application PCT/US90/05565. The latter four documents are hereby incorporated by reference.

In particular embodiments, fluorophores that can be used as detectable labels for probes include, but are not limited to, rhodamine, cyanine 3 (Cy 3), cyanine 5 (Cy 5), fluorescein, Vic™, Liz™, Tamra™, 5-Fam™, 6-Fam™, 6-HEX, CAL Fluor Green 520, CAL Fluor Gold 540, CAL Fluor Orange 560, CAL Fluor Red 590, CAL Fluor Red 610, CAL Fluor Red 615, CAL Fluor Red 635, and Texas Red (Molecular Probes). (Vic™, Liz™, Tamra™, 5-Fam™, 6-Fam™ are all available from Applied Biosystems, Foster City, Calif. 6-HEX and CAL Fluor dyes are available from Biosearch Technologies).

In particular embodiments, molecules useful as quenchers include, but are not limited to tetramethylrhodamine (TAMRA), DABCYL (DABSYL, DABMI or methyl red) anthroquinone, nitrothiazole, nitroimidazole, malachite green, Black Hole Quenchers®, e.g., BHQ1 (Biosearch Technologies), Iowa Black® or ZEN quenchers (from Integrated DNA Technologies, Inc.), TIDE Quencher 2 (TQ2) and TIDE Quencher 3 (TQ3) (from AAT Bioquest).

There are many linking moieties and methodologies for attaching reporter or quencher molecules to the 5' or 3' termini of oligonucleotides, as exemplified by the following references: Eckstein, editor, Oligonucleotides and Analogues: A Practical Approach (IRL Press, Oxford, 1991); Zuckerman et al., Nucleic Acids Research, 15: 5305-5321 (1987) (3' thiol group on oligonucleotide); Sharma et al., Nucleic Acids Research, 19: 3019 (1991) (3' sulfhydryl); Giusti et al., PCR Methods and Applications, 2: 223-227 (1993) and Fung et al., U.S. Pat. No. 4,757,141 (5' phosphoamino group via Aminolink™ II available from Applied Biosystems, Foster City, Calif.) Stabinsky, U.S. Pat. No. 4,739,044 (3' aminoalkylphosphoryl group); Agrawal et al., Tetrahedron Letters, 31: 1543-1546 (1990) (attachment via phosphoramidate linkages); Sproat et al., Nucleic Acids Research, 15: 4837 (1987)

(5' mercapto group); Nelson et al., Nucleic Acids Research, 17: 7187-7194 (1989) (3' amino group); and the like.

Preferably, commercially available linking moieties are employed that can be attached to an oligonucleotide during synthesis, e.g., available from Integrated DNA Technologies (Coralville, Iowa) or Eurofins MWG Operon (Huntsville, Ala.).

Rhodamine and fluorescein dyes are also conveniently attached to the 5' hydroxyl of an oligonucleotide at the conclusion of solid phase synthesis by way of dyes derivatized with a phosphoramidite moiety, e.g., Woo et al., U.S. Pat. No. 5,231,191; and Hobbs, Jr., U.S. Pat. No. 4,997,928.

By judicious choice of labels, analyses can be conducted in which the different labels are excited and/or detected at different wavelengths in a single reaction. See, e.g., Fluorescence Spectroscopy (Pesce et al., Eds.) Marcel Dekker, New York, (1971); White et al., Fluorescence Analysis: A Practical Approach, Marcel Dekker, New York, (1970); Berlman, Handbook of Fluorescence Spectra of Aromatic Molecules, 2nd ed., Academic Press, New York, (1971); Griffiths, Colour and Constitution of Organic Molecules, Academic Press, New York, (1976); Indicators (Bishop, Ed.). Pergamon Press, Oxford, 19723; and Haugland, Handbook of Fluorescent Probes and Research Chemicals, Molecular Probes, Eugene (1992). The reporter and quencher molecules can be positioned on the probe oligonucleotide and the regulatory oligonucleotide strategically for a desired distance between these labels. Typically, the distance between the reporter and quencher molecules will be minimized to increase the effectiveness of the quencher molecule. The location of the reporter and quencher molecules can be chosen strategically such that upon hybridization of the probe oligonucleotide to the regulatory oligonucleotide, the reporter and quencher molecules are less than 20 nm, 10 nm, 7.5 nm, 6 nm, 5 nm, 4 nm, 3 nm, 1 nm, 0.8 nm, 0.6 nm, 0.4 nm or less apart. Preferably, the reporter and quencher molecules can be positioned at complementary nucleotides in the context of an probe oligonucleotide/regulatory oligonucleotide hybridization along the regulatory sequence. More preferably, the reporter and the quencher molecules can be positioned at the 5' end of the oligonucuelotide probe and the 3' end of the regulatory olignucleotide.

Amplification Methods
In General

In illustrative embodiments, the same set of target nucleic acids can be amplified in each of two or more different samples. The samples can differ from one another in any way, e.g., the samples can be from different tissues, subjects, environmental sources, etc.

The probe oligonucleotide can be provided in the amplification mixture in varying abundance compared to that of the tagging primer and/or reverse primer(s). More specifically, probe oligonucleotide can be present in excess of the tagging primer. The reverse primer in the amplification mixture, can be present, in illustrative embodiments, at a concentration in excess of the tagging primer. For example, the concentration of the probe oligonucleotide in the amplification mixtures can be at least 1.5-fold, at least 4-fold, at least 5-fold, at least 10-fold, at least 15-fold, at least 20-fold, at least 25-fold, at least 30-fold, at least 35-fold, at least 40-fold, at least 45-fold, at least 50-fold, at least 100-fold, at least 500-fold, at least $10^3$-fold, at least $5 \times 10^3$-fold, at least $10^4$-fold, at least $5 \times 10^4$-fold, at least $10^5$-fold, at least $5 \times 10^5$-fold, at least $10^6$-fold, or higher, relative to the concentration of the tagging and/or reverse primer(s). In illustrative embodiments, the tagging primer can be present in picomolar to nanomolar concentrations, e.g., about 500 nM to 5 µM, about 100 nM to 5 µM, about 50 nM to 5 µM, about 10 nM to 5 µM, about 5 nM to 5 µM, about 1 nM to 10 µM, about 50 µM to about 500 µM, about 100 µM or any other range having any of these values as endpoints (e.g., 10 nM to 50 µM). Suitable, illustrative concentrations of probe oligonucleotide that could be used on combination with any of these concentrations of forward primer include about 10 nM to about 10 µM, about 25 nM to about 7.5 µM, about 50 nM to about 5 µM, about 75 nM to about 2.5 µM, about 100 nM to about 1 µM, about 250 nM to about 750 nM, about 500 nM or any other range having any of these values as endpoints (e.g., 10 nM to 50 µM).

Each amplification mixture can be subjected to amplification to produce target amplicons comprising tagged target nucleotide sequences comprising the nucleotide tag. In certain embodiments, the nucleotide tag is selected so as to avoid substantial annealing to the target nucleic acids. In such embodiments, the tagged target nucleotide sequences can include molecules having the following elements: 5'-(nucleotide tag from the tagging primer)-(target nucleotide sequence)-3'.

In illustrative embodiments, the nucleotide tag sequence identifies a particular polymorphic variant. Thus, for example, a set of T target nucleic acids, each containing S polymorphic variants, can be amplified, where S and T are integers, typically greater than one. In such embodiments, amplification can be performed separately for each target nucleic acid, wherein a different tagging primer is used for each polymorphic variant. A different probe oligonucleotide with a corresponding nucleotide tag can be used for each polymorphic variant. This embodiment has the advantage of reducing the number of different probe oligonucleotides that would need to be synthesized to identify polymorphic variance in amplicons produced for a plurality of target sequences. Alternatively, different sets of tagging and reverse primers can be employed for each target, wherein each set has a set of nucleotide tags for each polymorphic variant that is different from the primers in the other set, and different probe oligonucleotides are used for each sample, wherein the probe oligonucleotides have the corresponding sets of nucleotide tag sequences and different reporter molecules. In either case, the amplification produces a set of T amplicons from each sample that bear allele-specific reporters. Regulatory oligonucleotides specifically recognizing the different regulatory sequences in each probe oligonucleotide are provided with a corresponding quencher molecule.

In embodiments, wherein the same set of tagging and reverse primers is used for each sample, the tagging and reverse primers for each target can be initially combined separately from the sample, and each probe oligonucleotide/regulatory oligonucleotide set can be initially combined with its corresponding sample. Aliquots of the initially combined tagging and reverse primers can then be added to aliquots of the initially combined sample and probe oligonucleotide/regulatory oligonucleotide sets. These amplification mixtures can be formed in any article that can be subjected to conditions suitable for amplification. For example, the amplification mixtures can be formed in, or distributed into, separate compartments of a microfluidic device prior to amplification. Suitable microfluidic devices include, in illustrative embodiments, matrix-type microfluidic devices, such as those described below.

Any amplification method can be employed to produce amplicons from the amplification mixtures. In illustrative embodiments, PCR is employed.

PCR thermal cycling protocols are well known in the art. Typically, PCR consists of a series of 20-40 cycles. For example, and not limitation the cycle may include a denaturation step, an annealing step (allowing annealing of the primers to the single-stranded DNA template) and an extension/elongation step.

The amplification is generally carried out for at least three cycles to introduce the nucleotide tag. In various embodiments, amplification is carried out for 5, 10, 15, 20, 25, 30, 35, 40, 45, or 50 cycles, or for any number of cycles falling within a range having any of these values as endpoints (e.g. 5-10 cycles). In particular embodiments, amplification is carried out for a sufficient number of cycles to normalize target amplicon copy number across targets and across samples (e.g., 15, 20, 25, 30, 35, 40, 45, or 50 cycles, or for any number of cycles falling within a range having any of these values as endpoints).

An exemplary protocol, for illustration and not limitation, includes a hotstart step [95° C. for 5 min], a 35 cycle touchdown PCR strategy [1 cycle of 95° C. for 15 sec, 64° C. for 45 sec, and 72° C. for 15 sec; 1 cycle of 95° C. for 15 sec, 63° C. for 45 sec, and 72° C. for 15 sec; 1 cycle of 95° C. for 15 sec, 62° C. for 45 sec, and 72° C. for 15 sec; 1 cycle of 95° C. for 15 sec, 61° C. for 45 sec, and 72° C. for 15 sec; and 34 cycles of 95° C. for 15 sec, 62° C. for 45 sec, and 72° C. for 15 sec], and a cooling step [1 cycle of 25° C. for 10 sec].

Particular embodiments of the above-described method provide substantially uniform amplification, yielding one or more target amplicons wherein the majority of amplicons are present at a level relatively close to the average copy number calculated for the one or more target amplicons. Thus, in various embodiments, at least 50, at least 55, at least 60, at least 65, at least 70, at least 75, at least 80, at least 85, at least 90, at least 91, at least 92, at least 93, at least 94, at least 95, at least 96, at least 97, at least 98, or at least 99 percent of the target amplicons are present at greater than 50 percent of the average number of copies of target amplicons and less than 2-fold the average number of copies of target amplicons.

The invention also provides, in certain embodiments, a method for amplifying a plurality of target nucleotides in which the incorporation of the probe oligonucleotide is, optionally, omitted and the target nucleotide sequences are tagged during the amplification. More specifically, the invention provides a method for amplifying a plurality of target nucleic acids, typically, in a plurality of samples, that entails preparing an amplification mixture for each target nucleic acid. Each amplification mixture includes a tagging primer including a target-specific sequence and a reverse primer including a target-specific sequence. The amplification mixtures are subjected to amplification to produce amplicons of one or more target nucleotides. The target nucleotide sequences are then provided one or more sets of probe oligonucleotide/regulatory oligonucleotide, wherein the probe oligonucleotides recognize the nucleotide tag associated with each polymorphic variant. In various embodiments, a second amplification reaction can be performed to incorporate the probe oligonucleotide. In alternative embodiments, the probe oligonucleotide hybridizes to the tagged target nucleic acid, wherein the regulatory oligonucleotide acts as a competing agent. In such embodiments, it will be especially advantageous for the regulatory oligonucleotide to have an auxiliary sequence that partially overlaps with the nucleotide tag recognition sequence on the probe oligonucleotide. It will be further advantageous for the auxiliary sequence to have a reduced complementarity to the probe oligonucleotide, compared to the tagged target nucleic acid along the same nucleotides, when the probe oligonucleotide and the regulatory oligonucleotide are aligned along the regulatory sequence. In preferred embodiments, this auxiliary sequence will be located at the 5' end of the regulatory oligonucleotide.

The competitiveness of the regulatory oligonucleotide for the probe oligonucleotide can be adjusted varying the strength of the interaction between the regulatory oligonucleotide and the probe oligonucleotide, as well as the interaction between the nucleotide tag and the probe oligonucleotide. The competition can be standardized such that the acquired signal is relatively proportional to the average copy number of a tagged target nucleic acid with a particular polymorphic variant.

Long-Range PCR

In various embodiments, the target nucleotide sequence amplified can be, e.g., 25 bases, 50 bases, 100 bases, 200 bases, 500 bases, or 750 bases. In certain embodiments of the above-described methods, a long-range amplification method, such as long-range PCR can be employed to produce amplicons from the amplification mixtures. Long-range PCR permits the amplification of target nucleotide sequences ranging from one or a few kilobases (kb) to over 50 kb. In various embodiments, the target nucleotide sequences that are amplified by long-range PCR are at least about 1, 2, 3, 4, 5, 6, 7, 8, 9, 10, 11, 12, 13, 14, 15, 20, 25, 30, 35, 40, 45, or 50 kb in length. Target nucleotide sequences can also fall within any range having any of these values as endpoints (e.g., 25 bases to 100 bases or 5-15 kb). The use of long-range PCR in the above-described methods can, in some embodiments, yield a plurality of target amplicons wherein at least 50, at least 55, at least 60, at least 65, or at least 70 percent of the target amplicons are present at greater than 50 percent of the average number of copies of target amplicons and less than 2-fold the average number of copies of target amplicons.

Long-range PCR is well known in the art. See, e.g., Cheng S, Fockler C, Barnes W M, Higuchi R (June 1994). "Effective amplification of long targets from cloned inserts and human genomic DNA". Proc. Natl. Acad. Sci. U.S.A. 91 (12): 5695-9. Enzymes, protocols, and kits for long-range PCR that are suitable for use in the methods described here are commercially available; examples include: SequalPrep™ Long PCR Kit (Invitrogen, USA), PfuUltra® II Fusion HS DNA polymerase (Stratagene), Phusion® DNA polymerases, Phusion® Flash High Fidelity PCR Master Mix (Finnzymes).

In certain embodiments, the amount of target amplicons produced in the amplification mixtures can be quantified during amplification, e.g., by quantitative real-time PCR, or after.

Digital PCR

In some embodiments, samples are loaded into an amplification device, for example, a PCR plate or a microfluidic device, at sample concentrations containing on average in the range of 0.8 to 1.6 amplification templates per well, or in some embodiments one amplification template per well or chamber. Each well or chamber in the device is prepared such that it contains suitable tagging and reverse primers and a relevant combination of probe oligonucleotide/regulatory oligonucleotide sets. For discussions of "digital PCR" see, for example, Vogelstein and Kinzler, 1999, *Proc Natl Acad Sci USA* 96:9236-41; McBride et al., U.S Patent Application Publication No. 20050252773, especially Example 5 (each of these publications are hereby incorporated by reference in their entirety). Digital amplification methods can make use of certain-high-throughput devices suitable for digital PCR, such as microfluidic devices typically including a large number and/or high density of small-volume reaction sites (e.g., nano-volume reaction sites or reaction chambers). In illustrative embodiments, digital amplification is performed using a microfluidic device, such as the Digital Array microfluidic devices described below. Digital amplification can entail distributing or partitioning a sample among hundreds to thousands of reaction mixtures disposed in a reaction/assay platform or microfluidic device. In counting the number of positive amplification results, e.g, at the reaction endpoint, one is counting the individual template molecules present in the input sample one-by-one. A major advantage of digital amplification is that the quantification is independent of variations in the amplification efficiency—successful amplifications are counted as one molecule, independent of the actual amount of product.

In certain embodiments, digital amplification can be carried out after preamplification of sample nucleic acids. Typically, preamplification prior to digital amplification is performed for a limited number of thermal cycles (e.g., 5 cycles, or 10 cycles). In certain embodiments, the number of thermal cycles during preamplification can range from about 4 to 15 thermal cycles, or about 4-10 thermal cycles. In certain embodiments the number of thermal cycles can be 3, 4, 5, 6, 7, 8, 9, 10, 11, 12, 13, 14, 15, or more than 15. The above-described amplification to produce adaptor sequence-containing amplicons for DNA sequencing can be substituted for the typical preamplification step.

Digital amplification methods are described in U.S. Publication No. 20090239308, which is hereby incorporated by reference in its entirety and, in particular, for its disclosure of digital amplification methods and devices. Generally, in digital amplification, identical (or substantially similar) amplification reactions are run on a nucleic acid sample, such as genomic DNA. The number of individual reactions for a given nucleic acid sample may vary from about 2 to over 1,000,000. Typically, the number of reactions performed on a sample is about 100 or greater, more typically about 200 or greater, and even more typically about 300 or greater. Larger scale digital amplification can also be performed in which the number of reactions performed on a sample is about 500 or greater, about 700 or greater, about 765 or greater, about 1,000 or greater, about 2,500 or greater, about 5,000 or greater, about 7,500 or greater, or about 10,000 or greater. The number of reactions performed may also be significantly higher, such up to about 25,000, up to about 50,000, up to about 75,000, up to about 100,000, up to about 250,000, up to about 500,000, up to about 750,000, up to about 1,000,000, or even greater than 1,000,000 assays per genomic sample.

In particular embodiments, the quantity of nucleic acid subjected to digital amplification is generally selected such that, when distributed into discrete reaction mixtures, each individual amplification reaction is expected to include one or fewer amplifiable nucleic acids. One of skill in the art can determine the concentration of target amplicon(s) produced as described above and calculate an appropriate amount for use in digital amplification. More conveniently, a set of serial dilutions of the target amplicon(s) can be tested. For example, a device that is commercially available from Fluidigm Corp. as the 12.765 Digital Array microfluidic device allows 12 different dilutions to be tested simultaneously. Optionally, a suitable dilution can be determined by generating a linear regression plot. For the optimal dilution, the line should be straight and pass through the origin. Subsequently the concentration of the original samples can be calculated from the plot.

The appropriate quantity of target amplicon(s) can be distributed into discrete locations or reaction wells or chambers such that each reaction includes, for example, an average of no more than about one amplicon per volume. The target amplicon(s) can be combined with (an) probe oligonucleotide/regulatory oligonucleotide set(s), prior to distribution or after.

Following distribution, the reaction mixtures are subjected to amplification to identify those reaction mixtures that contained a target amplicon. Any amplification method can be employed, but conveniently, PCR is used, e.g., real-time PCR or endpoint PCR. This amplification can employ probe oligonucleotides capable of amplifying the target amplicon(s). In particular embodiments, all or some of the probe oligonucleotide, regulatory oligonucleotide, tagging primer and reverse primer are provided. In alternative embodiments, the probe oligonucleotide can anneal to the nucleotide tag introduced in a previous amplification step.

The concentration of any target amplicon (copies/µl) is correlated with the number of positive (i.e., amplification product-containing) reaction mixtures. See U.S. patent publication No. 20090239308, which is incorporated by reference for all purposes and, in particular, for analysis of digital PCR results. Also see Dube et al., 2008, "Mathematical Analysis of Copy Number Variation in a DNA Sample Using Digital PCR on a Nanofluidic Device" PLoS ONE 3(8): e2876. doi:10.1371/journal.pone.0002876, which is incorporated by reference for all purposes and, in particular, for analysis of digital PCR results.

In an illustrative embodiment of sample calibration for DNA sequencing by digital PCR, a PCR reaction mix containing roughly 100-360 amplicons per µl can be loaded onto a Digital Array microfluidic device, such as Fluidigm Corporation's (South San Francisco, Calif.) 12.765 Digital Array microfluidic device, described below. The microfluidic chip has 12 panels and each panel contains 765 chambers. Replicate panels on the digital chip can be assayed in order to obtain absolute quantification of the initial concentration of a target nucleic acid.

Sample Nucleic Acids

Preparations of nucleic acids ("samples") can be obtained from biological sources and prepared using conventional methods known in the art. In particular, DNA or RNA useful in the methods described herein can be extracted and/or amplified from any source, including bacteria, protozoa, fungi, viruses, organelles, as well higher organisms such as plants or animals, particularly mammals, and more particularly humans. Suitable nucleic acids can also be obtained from environmental sources (e.g., pond water, air sample), from man-made products (e.g., food), from forensic samples, and the like. Nucleic acids can be extracted or amplified from cells, bodily fluids (e.g., blood, a blood fraction, urine, etc.), or tissue samples by any of a variety of standard techniques. Illustrative samples include samples of plasma, serum, spinal fluid, lymph fluid, peritoneal fluid, pleural fluid, oral fluid, and external sections of the skin; samples from the respiratory, intestinal genital, and urinary tracts; samples of tears, saliva, blood cells, stem cells, or tumors. For example, samples of fetal DNA can be obtained from an embryo or from maternal blood. Samples can be obtained from live or dead organisms or from in vitro cultures. Illustrative samples can include single cells, paraffin-embedded tissue samples, and needle biopsies. Nucleic acids useful in the invention can also be derived from one or more nucleic acid libraries, including cDNA, cosmid, YAC, BAC, P1, PAC libraries, and the like.

Nucleic acids of interest can be isolated using methods well known in the art, with the choice of a specific method depending on the source, the nature of nucleic acid, and similar factors. The sample nucleic acids need not be in pure form, but are typically sufficiently pure to allow the amplification steps of the methods of the invention to be performed. Where the target nucleic acids are RNA, the RNA can be reversed transcribed into cDNA by standard methods known in the art and as described in Sambrook, J., Fritsch, E. F., and Maniatis, T., *Molecular Cloning: A Laboratory Manual*. Cold Spring Harbor Laboratory Press, NY, Vol. 1, 2, 3 (1989), for example. The cDNA can then be analyzed according to the methods of the invention.

Target Nucleic Acids

Any target nucleic acid that can be tagged in an encoding reaction of the invention (described herein) can be detected using the methods of the invention. In typical embodiments, at least some nucleotide sequence information will be known for the target nucleic acids. For example, if the encoding reaction employed is PCR, sufficient sequence information is generally available for each end of a given target nucleic acid to permit design of suitable amplification primers. In an alternative embodiment, the target-specific sequences in primers could be replaced by random or degenerate nucleotide sequences.

The targets can include, for example, nucleic acids associated with pathogens, such as viruses, bacteria, protozoa, or fungi; RNAs, e.g., those for which over- or under-expression is indicative of disease, those that are expressed in a tissue- or developmental-specific manner; or those that are induced by particular stimuli; genomic DNA, which can be analyzed for specific polymorphisms (such as SNPs), alleles, or haplotypes, e.g., in genotyping. Of particular interest are genomic DNAs that are altered (e.g., amplified, deleted, and/or mutated) in genetic diseases or other pathologies; sequences that are associated with desirable or undesirable traits; and/or sequences that uniquely identify an individual (e.g., in forensic or paternity determinations).

Primer Design

Primers suitable for nucleic acid amplification are sufficiently long to prime the synthesis of extension products in the presence of the agent for polymerization. The exact length and composition of the primer will depend on many factors, including, for example, temperature of the annealing reaction, source and composition of the primer, and where a probe is employed, the nucleotide tag portion of the tagging primer will be designed applying the same principles to the annealing of the probe oligonucleotide to the nucleotide tag. The ratio of primer:probe concentration can also be considered. For example, depending on the complexity of the target nucleic acid sequence, an oligonucleotide primer typically contains in the range of about 15 to about 30 nucleotides that recognize the targeted nucleotide sequence, although it may contain more or fewer nucleotides. The primers should be sufficiently complementary to selectively anneal to their respective strands and form stable duplexes. One skilled in the art knows how to select appropriate primer pairs to amplify the target nucleic acid of interest.

Primers may be prepared by any suitable method, including, for example, cloning and restriction of appropriate sequences or direct chemical synthesis by methods such as the phosphotriester method of Narang et al. (1979) *Meth. Enzymol.* 68: 90-99; the phosphodiester method of Brown et al. (1979) *Meth. Enzymol.* 68: 109-151; the diethylphosphoramidite method of Beaucage et al. (1981) *Tetra. Lett.,* 22: 1859-1862; the solid support method of U.S. Pat. No. 4,458, 066 and the like, or can be provided from a commercial source.

Primers may be purified by using a Sephadex column (Amersham Biosciences, Inc., Piscataway, N.J.) or other methods known to those skilled in the art. Primer purification may improve the sensitivity of the methods of the invention.

Assay Formats

Assays of the invention may be carried ou in a variety of formats, including multiwell formats and microfluidic formats such as, but not limited to, droplet systems (see, e.g., Kiss et al., 2008, *Anal Chem* 80: 8975-81.) and integrated microfluidic devices. In some embodiments the PCR amplification reaction is carried out in a reaction volume greater than 500 nL, or greater than 1 uL. For example, in some embodiments the PCR amplification reactions are carried out in a multiwell plate comprising 96-1536 wells. In some embodiments, Ta is about 57° C. In other embodiments, the PCR amplification reaction is carried out in a reaction volume less than 100 nL. In some embodiments the PCR amplification reaction is carried out in a microfluidic device. In some embodiments Ta is about 60° C.

Microfluidic Devices

In certain embodiments, any of the methods of the invention can be carried out using a microfluidic device. In illustrative embodiments, the device is a matrix-type microfluidic device is one that allows the simultaneous combination of a plurality of substrate solutions with reagent-solutions in separate isolated reaction chambers. It will be recognized, that a substrate solution can comprise one or a plurality of substrates and a reagent solution can comprise one or a plurality of reagents. For example, the microfluidic device can allow the simultaneous pairwise combination of a plurality of different amplification primers and samples. In certain embodiments, the device is configured to contain a different combination of primers and samples in each of the different chambers. In various embodiments, the number of separate reaction chambers can be greater than 50, usually greater than 100, more often greater than 500, even more often greater than 1000, and sometimes greater than 5000, or greater than 10,000.

In particular embodiments, the matrix-type microfluidic device is a Dynamic Array ("DA") microfluidic device, an example of which is shown in FIG. 21 of WO 05/107938A2, and described therein. DA microfluidic device is a matrix-type microfluidic device designed to isolate pair-wise combinations of samples and reagents (e.g., amplification primers, detection probes, etc.) and suited for carrying out qualitative and quantitative PCR reactions including real-time quantitative PCR analysis. In some embodiments, the DA microfluidic device is fabricated, at least in part, from an elastomer. DA microfluidic devices are described in PCT publication WO05/107938A2 (Thermal Reaction Device and Method For Using The Same) and US Pat. Publication US20050252773A1, both incorporated herein by reference in their entireties for their descriptions of DA microfluidic devices. DA microfluidic devices may incorporate high-density matrix designs that utilize fluid communication vias between layers of the microfluidic device to weave control lines and fluid lines through the device and between layers. By virtue of fluid lines in multiple layers of an elastomeric block, high density reaction cell arrangements are possible. Alternatively DA microfluidic devices may be designed so that all of the reagent and sample channels are in the same elastomeric layer, with control channels in a different layer.

U.S. Patent Publication No. 2008/0223721 and PCT Publication No. WO 05/107938A2, both incorporated by reference herein, describe illustrative matrix-type devices that can be used to practice the methods described herein. FIG. 21 of WO 05/107938A2 shows an illustrative matrix design having a first elastomeric layer 2110 (1st layer) and a second elastomeric layer 2120 (2 d layer) each having fluid channels formed therein. For example, a reagent fluid channel in the first layer 2110 is connected to a reagent fluid channel in the second layer 2120 through a via 2130, while the second layer 2120 also has sample channels therein, the sample channels and the reagent channels terminating in sample and reagent chambers 2180, respectively. The sample and reagent chambers 2180 are in fluid communication with each other through an interface channel 2150 that has an interface valve 2140 associated therewith to control fluid communication between each of the chambers 2180 of a reaction cell 2160. In use, the interface is first closed, then reagent is introduced into the reagent channel from the reagent inlet and sample is introduced into the sample channel through the sample inlet; containment valves 2170 are then closed to isolate each reaction cell 2160 from other reaction cells 2160. Once the reaction cells 2160 are isolated, the interface valve 2140 is opened to cause the sample chamber and the reagent chamber to be in fluid communication with each other so that a desired reaction may take place. It will be apparent from this (and the description in WO 05/107938A2) that the DA microfluidic device may be used for reacting M number of different samples with N number of different reagents.

Although the DA microfluidic devices described above in WO 05/107938 are well suited for conducting the methods described herein, the invention is not limited to any particular device or design. Any device that partitions a sample and/or allows independent pair-wise combinations of reagents and sample may be used. U.S. Patent Publication No. 20080108063 (which is hereby incorporated by reference it its entirety) includes a diagram illustrating the 48.48 Dynamic Array IFC (Integrated Fluidic Circuit), a commercially available device available from Fluidigm Corp. (South San Francisco Calif.).

It will be understood that other configurations are possible and contemplated such as, for example, 48×96; 96×96; 30×120; etc.

In specific embodiments, the microfluidic device can be a Digital Array microfluidic device, which is adapted to perform digital amplification. Such devices can have integrated channels and valves that partition mixtures of sample and reagents into nanolitre volume reaction chambers. In some embodiments, the Digital Array microfluidic device is fabricated, at least in part, from an elastomer. Illustrative Digital Array microfluidic devices are described in pending U.S. applications owned by Fluidigm, Inc., such as U.S. patent publication No. 20090239308. One illustrative embodiment has 12 input ports corresponding to 12 separate sample inputs to the device. The device can have 12 panels, and each of the 12 panels can contain 765 6 nL reaction chambers with a total volume of 4.59 µl it per panel. Microfluidic channels can connect the various reaction chambers on the panels to fluid sources. Pressure can be applied to an accumulator in order to open and close valves connecting the reaction chambers to fluid sources. In illustrative embodiments, 12 inlets can be provided for loading of the sample reagent mixture. 48 inlets can be used to provide a source for reagents, which are supplied to the biochip when pressure is applied to accumulator. Additionally, two or more inlets can be provided to provide hydration to the biochip. Hydration inlets are in fluid communication with the device to facilitate the control of humidity associated with the reaction chambers. As will be understood to one of skill in the art, some elastomeric materials that can be utilized in the fabrication of the device are gas permeable, allowing evaporated gases or vapor from the reaction chambers to pass through the elastomeric material into the surrounding atmosphere. In a particular embodiment, fluid lines located at peripheral portions of the device provide a shield of hydration liquid, for example, a buffer or master mix, at peripheral portions of the biochip surrounding the panels of reaction chambers, thus reducing or preventing evaporation of liquids present in the reaction chambers. Thus, humidity at peripheral portions of the device can be increased by adding a volatile liquid, for example water, to hydration inlets. In a specific embodiment, a first inlet is in fluid communication with the hydration fluid lines surrounding the panels on a first side of the biochip and the second inlet is in fluid communication with the hydration fluid lines surrounding the panels on the other side of the biochip.

While the Digital Array microfluidic devices are well-suited for carrying out the digital amplification methods described herein, one of ordinary skill in the art would recognize many variations and alternatives to these devices. The microfluidic device which is the 12.765 Dynamic Array commercially available from Fluidigm Corp. (South San Francisco, Calif.), includes 12 panels, each having 765 reaction chambers with a volume of 6 nL per reaction chamber. However, this geometry is not required for the digital amplification methods described herein. The geometry of a given Digital Array microfluidic device will depend on the particular application. Additional description related to devices suitable for use in the methods described herein is provided in U.S. Patent Application Publication No. 2005/0252773, incorporated herein by reference for its disclosure of Digital Array microfluidic devices.

In certain embodiments, the methods described herein can be performed using a microfluidic device that provides for recovery of reaction products. Such devices are described in detail in copending U.S. Application No. 61/166,105, filed Apr. 2, 2009, which is hereby incorporated by reference in its entirety and specifically for its description of microfluidic devices that permit reaction product recovery and related methods.

Detection

In particular embodiments, real-time quantification methods are used. For example, "quantitative real-time PCR" methods can be used to determine the quantity of a target nucleic acid present in a sample by measuring the amount of amplification product formed during the amplification process itself. This method of monitoring the formation of amplification product involves the measurement of PCR product accumulation at multiple time points.

Devices have been developed that can perform a thermal cycling reaction with compositions containing a fluorescent indicator, emit a light beam of a specified wavelength, read the intensity of the fluorescent dye, and display the intensity of fluorescence after each cycle. Devices comprising a thermal cycler, light beam emitter, and a fluorescent signal detector, have been described, e.g., in U.S. Pat. Nos. 5,928,907; 6,015,674; and 6,174,670.

In some embodiments, each of these functions can be performed by separate devices. For example, if one employs a Q-beta replicase reaction for amplification, the reaction may not take place in a thermal cycler, but could include a light beam emitted at a specific wavelength, detection of the fluorescent signal, and calculation and display of the amount of amplification product.

In particular embodiments, combined thermal cycling and fluorescence detecting devices can be used for precise quantification of target nucleic acids. In some embodiments, fluorescent signals can be detected and displayed during and/or after one or more thermal cycles, thus permitting monitoring of amplification products as the reactions occur in "real-time." In certain embodiments, one can use the amount of amplification product and number of amplification cycles to calculate how much of the target nucleic acid sequence was in the sample prior to amplification.

According to some embodiments, one can simply monitor the amount of amplification product after a predetermined number of cycles sufficient to indicate the presence of the target nucleic acid sequence in the sample. One skilled in the art can easily determine, for any given sample type, primer sequence, and reaction condition, how many cycles are sufficient to determine the presence of a given target nucleic acid.

The detection is typically performed under conditions favorable for the association of the reporter and quencher molecules. A suitable temperature can be chosen to improve the hybridization of the probe oligonucleotide and the regulatory oligonucleotide for signal acquisition. In particular embodiments, the acquisition temperature is chosen such that a significant fraction of the unincorporated probe oligonucleotide is hybridized with the regulatory oligonucleotide. This significant fraction limit can be determined according to ranges specified elsewhere in this application.

According to certain embodiments, one can employ an internal standard to quantify the amplification product indicated by the fluorescent signal. See, e.g., U.S. Pat. No. 5,736,333.

In various embodiments, employing preamplification, the number of preamplification cycles is sufficient to add one or more nucleotide tags to the target nucleotide sequences, so that the relative copy numbers of the tagged target nucleotide sequences is substantially representative of the relative copy numbers of the target nucleic acids in the sample. For example, preamplification can be carried out for 2-20 cycles to introduce the sample-specific nucleotide tags. In other embodiments, detection is carried out at the end of exponential amplification, i.e., during the "plateau" phase, or endpoint PCR is carried out. In this instance, preamplification will normalize amplicon copy number across targets and across samples. In various embodiments, preamplification and/or amplification can be carried out for about: 2, 4, 10, 15, 20, 25, 30, 35, or 40 cycles or for a number of cycles falling within any range bounded by any of these values.

Removal of Undesired Reaction Components

It will be appreciated that reactions involving complex mixtures of nucleic acids in which a number of reactive steps are employed can result in a variety of unincorporated reaction components, and that removal of such unincorporated reaction components, or reduction of their concentration, by any of a variety of clean-up procedures can improve the efficiency and specificity of subsequently occurring reactions. For example, it may be desirable, in some embodiments, to remove, or reduce the concentration of preamplification primers or tagging primers prior to carrying out the amplification steps described herein.

In certain embodiments, the concentration of undesired components can be reduced by simple dilution. For example, preamplified samples can be diluted about 2-, 5-, 10-, 50-, 100-, 500-, 1000-fold prior to amplification to improve the specificity of the subsequent amplification step.

In some embodiments, undesired components can be removed by a variety of enzymatic means. Alternatively, or in addition to the above-described methods, undesired components can be removed by purification. For example, a purification tag can be incorporated into any of the above-described primers (e.g., into the barcode nucleotide sequence) to facilitate purification of the tagged target nucleotides.

In particular embodiments, clean-up includes selective immobilization of the desired nucleic acids. For example, desired nucleic acids can be preferentially immobilized on a solid support. In an illustrative embodiment, an affinity moiety, such as biotin (e.g., photo-biotin), is attached to desired nucleic acid, and the resulting biotin-labeled nucleic acids immobilized on a solid support comprising an affinity moiety-binder such as streptavidin. Immobilized nucleic acids can be queried with probes, and non-hybridized and/or non-ligated probes removed by washing (See, e.g., Published P.C.T. Application WO 03/006677 and US Patent Publication No. 20030036064 Alternatively, immobilized nucleic acids can be washed to remove other components and then released from the solid support for further analysis. In particular embodiments, an affinity moiety, such as biotin, can be attached to an amplification primer such that amplification produces an affinity moiety-labeled (e.g., biotin-labeled) amplicon. Thus, for example, where a tagging primer, reverse primer and an probe oligonucleotide are employed, as described above, at least one of said oligonucleotides can include an affinity moiety.

Data Output and Analysis

In certain embodiments, when the methods of the invention are carried out on a matrix-type microfluidic device, the data can be output as a heat matrix (also termed "heat map"). In the heat matrix, each square, representing a reaction chamber on the matrix, has been assigned a color value which can be shown in gray scale, but is more typically shown in color. In gray scale, black squares indicate that no amplification product was detected, whereas white squares indicate the highest level of amplification produce, with shades of gray indicating levels of amplification product in between. In a further aspect, a software program may be used to compile the data generated in the heat matrix into a more reader-friendly format.

Applications

The methods of the invention are applicable to any technique aimed at detecting the presence or amount of one or more target nucleic acids in a nucleic acid sample. Thus, for example, these methods are applicable to identifying the presence of particular polymorphisms (such as SNPs), alleles, or haplotypes, or chromosomal abnormalities, such as amplifications, deletions, or aneuploidy. The methods may be employed in genotyping, which can be carried out in a number of contexts, including diagnosis of genetic diseases or disorders, pharmacogenomics (personalized medicine), quality control in agriculture (e.g., for seeds or livestock), the study and management of populations of plants or animals (e.g., in aquaculture or fisheries management or in the determination of population diversity), species or strain determination or paternity or forensic identifications. The methods of the invention can be applied in the identification of sequences indicative of particular conditions or organisms in biological or environmental samples. For example, the methods can be used in assays to identify pathogens, such as viruses, bacteria, and fungi). The methods can also be used in studies aimed at characterizing environments or microenvironments, e.g., characterizing the microbial species in the human gut.

These methods can also be employed in determinations DNA or RNA copy number. Determinations of aberrant DNA copy number in genomic DNA is useful, for example, in the diagnosis and/or prognosis of genetic defects and diseases, such as cancer. Determination of RNA "copy number," i.e., expression level is useful for expression monitoring of genes of interest, e.g., in different individuals, tissues, or cells under different conditions (e.g., different external stimuli or disease states) and/or at different developmental stages.

In addition, the methods can be employed to prepare nucleic acid samples for further analysis, such as, e.g., DNA sequencing. Diseases with a genetic component can be tested for carrier status or risk disease occurrence in subjects. One aspect of the invention relates to predicting the carrier status or the risk of disease occurrence in a subject. The list of diseases with a genetic component is growing and comprises Haemophilia, Galactosemia, Duchenne Muscular Dystrophy, Polycystic Kidney Disease, Neurofibromatosis Type I, Hereditary Spherocytosis, Marfan syndrome, Huntington's Disease, Abdominal Aortic Aneurysm, Age-related Macular Degeneration, Alcohol Dependence, Alopecia Areata, Ankylosing Spondylitis, Asthma, Atopic Dermatitis, Atrial Fibrillation, Atrial Fibrillation: Preliminary Research, Attention-Deficit Hyperactivity Disorder, Back Pain, Basal Cell Carcinoma, Behcet's Disease, Bipolar Disorder, Bipolar Disorder: Preliminary Research, Bladder Cancer, Brain Aneurysm, Breast Cancer, Celiac Disease, Chronic Kidney Disease, Chronic Lymphocytic Leukemia, Chronic Obstructive Pulmonary Disease (COPD), Cleft Lip and Cleft Palate, Cluster Headaches, Colorectal Cancer, Creutzfeldt-Jakob Disease, Crohn's Disease, Developmental Dyslexia, Endometriosis, Esophageal Cancer, Esophageal Squamous Cell Carcinoma (ESCC), Essential Tremor, Exfoliation Glaucoma, Follicular Lymphoma, Gallstones, Generalized Vitiligo, Gestational Diabetes, Gout, Hashimoto's Thyroiditis, Heart Attack, Hypertension, Hodgkin Lymphoma, Hypertriglyceridemia, Intrahepatic Cholestasis of Pregnancy, Keloid, Kidney Disease, Kidney Stones, Larynx Cancer, Lou Gehrig's Disease (ALS), Lung Cancer, Lupus (Systemic Lupus Erythematosus), Male Infertility, Melanoma, Multiple Sclerosis, Narcolepsy, Nasopharyngeal Carcinoma, Neural Tube Defects, Neuroblastoma, Nicotine Dependence, Nonalcoholic Fatty Liver Disease, Obesity, Obsessive-Compulsive Disorder, Oral and Throat Cancer, Osteoarthritis, Otosclerosis, Paget's Disease of Bone, Parkinson's Disease, Parkinson's Disease: Preliminary Research, Peripheral Arterial Disease, Placental Abruption, Polycystic Ovary Syndrome, Preeclampsia, Primary Biliary Cirrhosis, Progressive Supranuclear Palsy, Prostate Cancer, Psoriasis, Restless Legs Syndrome, Rheumatoid Arthritis, Schizophrenia, Limited Cutaneous Type Scleroderma, Selective IgA Deficiency, Sjögren's Syndrome, Stomach Cancer, Gastric Cardia Adenocarcinoma, Stroke, Tardive Dyskinesia, Thyroid Cancer, Tourette's Syndrome, Type 1 Diabetes, Type 2 Diabetes, Ulcerative Colitis, Uterine Fibroids, and Venous Thromboembolism, Alpha-1 Antitrypsin Deficiency, Cancer, Bloom's Syndrome, Canavan Disease, Connexin 26-Related Sensorineural Hearing Loss, Cystic Fibrosis, Factor XI Deficiency, Familial Dysautonomia, Familial Hypercholesterolemia Type B, Familial Mediterranean Fever, FANCC-related Fanconi Anemia, G6PD Deficiency, Gaucher Disease, Glycogen Storage Disease Type 1a, Hemochromatosis, Limb-girdle Muscular Dystrophy, Maple Syrup Urine Disease Type 1B, Mucolipidosis IV, Niemann-Pick Disease Type A, Phenylketonuria, Rhizomelic Chondrodysplasia Punctata Type 1 (RCDP1), Sickle Cell Anemia & Malaria Resistance, Tay-Sachs Disease, and Torsion Dystonia. Genotypes associated with genetic traits can also be tested in subjects. Yet another aspect of the invention relates to predicting the carrier status or the likelihood of occurrence of a trait in a subject. Genetic traits that are correlated with a genotype comprise Adiponectin Levels, Alcohol Flush Reaction, Asparagus Metabolite Detection, Avoidance of Errors, Birth Weight, Bitter Taste Perception, Blood Glucose, IQ Dependence on Breastfeeding, C-reactive Protein Level, Chronic Hepatitis B, Earwax Type, Eye Color, Food Preference, Freckling, HDL Cholesterol Level, HIV Progression, Hair Color, Hair Curl, Hair Thickness, Height, Hypospadias, Lactose Intolerance, Leprosy Susceptibility, Longevity, Susceptibility to Malaria Complications, Malaria Resistance (Duffy Antigen), Male Pattern Baldness, Non-verbal IQ, Obesity, Episodic Memory, Age at Menarche, Early Menopause, Muscle Performance, Diego, Kidd, and Kell Blood Groups, Norovirus Resistance, Odor Detection, Pain Sensitivity, Persistent Fetal Hemoglobin, Photic Sneeze Reflex, Prostate-Specific Antigen, Reading Ability, Refractive Error, Resistance to HIV/AIDS, Response to Diet and Exercise, Sex Hormone Regulation, Smoking Behavior, and Tuberculosis Susceptibility.

Further, an individual's response to treatment by a drug can be linked to particular genotypes. Another aspect of the invention relates to predicting an individual's response to drug treatment in correlation with a particular genotype. Drug responses can be predicted for a list of drug treatments comprising Alpha-1 Antitrypsin Deficiency, Breast Cancer, Bloom's Syndrome, Canavan Disease, Connexin 26-Related Sensorineural Hearing Loss, Cystic Fibrosis, Factor XI Deficiency, Familial Dysautonomia, Familial Hypercholesterolemia Type B, Familial Mediterranean Fever, FANCC-related Fanconi Anemia, G6PD Deficiency, Gaucher Disease, Glycogen Storage Disease Type 1a, Hemochromatosis, Limb-girdle Muscular Dystrophy, Maple Syrup Urine Disease Type 1B, Mucolipidosis IV, Niemann-Pick Disease Type A, Phenylketonuria, Rhizomelic Chondrodysplasia Punctata Type 1 (RCDP1), Sickle Cell Anemia & Malaria Resistance, Tay-Sachs Disease, and Torsion Dystonia.

Finally, nucleic acid samples can be tagged as a first step, prior subsequent analysis, to reduce the risk that mislabeling or cross-contamination of samples will compromise the results. For example, any physician's office, laboratory, or hospital could tag samples immediately after collection, and the tags could be confirmed at the time of analysis. Similarly, samples containing nucleic acids collected at a crime scene could be tagged as soon as practicable, to ensure that the samples could not be mislabeled or tampered with. Detection of the tag upon each transfer of the sample from one party to another could be used to establish chain of custody of the sample.

Kits

Kits according to the invention include one or more reagents useful for practicing one or more assay methods of the invention. A kit generally includes a package with one or more containers holding the reagent(s) (e.g., primers and/or probe(s)), as one or more separate compositions or, optionally, as admixture where the compatibility of the reagents will allow. The kit can also include other material(s) that may be desirable from a user standpoint, such as a buffer(s), a diluent(s), a standard(s), and/or any other material useful in sample processing, washing, or conducting any other step of the assay.

Kits according to the invention generally include instructions for carrying out one or more of the methods of the invention. Instructions included in kits of the invention can be affixed to packaging material or can be included as a package insert. While the instructions are typically written or printed materials they are not limited to such. Any medium capable of storing such instructions and communicating them to an end user is contemplated by this invention. Such media include, but are not limited to, electronic storage media (e.g., magnetic discs, tapes, cartridges, chips), optical media (e.g., CD ROM), RF tags, and the like. As used herein, the term "instructions" can include the address of an internet site that provides the instructions.

It is understood that the examples and embodiments described herein are for illustrative purposes only and that various modifications or changes in light thereof will be suggested to persons skilled in the art and are to be included within the spirit and purview of this application and scope of the appended claims.

In addition, all other publications, patents, and patent applications cited herein are hereby incorporated by reference in their entirety for all purposes.

EXAMPLES

Example 1

FIG. 1 illustrates use of the method in a genotyping assay, to detect the presence of specific allele(s) in a sample. In the cartoon, two target nucleic acid sequences (T and T') are present in the sample, T being characterized by an A allele at a particular SNP and T' being characterized by a G allele. T and T' are tagged in a PCR reaction using a pair of tagging primers, one comprising a nucleotide tag sequence X and a target nucleotide recognition sequence that hybridizes to, and acts as a primer for, the A allele, and the other comprising a nucleotide tag sequence Y and a target nucleotide recognition sequence that hybridizes to, and acts as a primer for, the G allele. The encoding or tagging PCR reaction (shown as an encoding PCR reaction) "incorporates" the x tag into amplicons (if any) of the A allele, and "incorporates" the y tag into amplicons (if any) of the G allele. The encoding amplification may make use of a single reverse primer.

As shown in the figure, the reaction contains two probe oligonucleotide-regulatory nucleotides pairs. In the first, the probe oligonucleotide comprises a reporter ($R_G$), a regulatory sequence (z), and a primer sequence that hybridizes to the tag sequence incorporated into the A allele amplicons and acts as primer for the PCR amplification reaction, while the regulatory oligonucleotide comprises a quencher (Q) and a sequence segment (z) complementary to regulatory sequence. In the second, the probe oligonucleotide comprises a reporter ($R_R$), a regulatory sequence (w), and a primer sequence that hybridizes to the tag sequence incorporated into the G allele amplicons and acts as primer for the PCR amplification reaction, while the regulatory oligonucleotide comprises a quencher (Q), which may be the same or different from the quencher of the first pair, and a sequence segment (w) complementary to regulatory sequence. The probe oligonucleotide and regulatory oligonucleotide of each pair comprise a reporter-quencher pair so that the reporter emits a detectable (e.g., fluorescent) signal when the probe oligonucleotide is hybridized to the regulatory oligonucleotide, but does not emit the signal when the probe and regulatory oligonucleotides are hybridized to each other, the reporter is quenched.

As is shown in the figure, probe oligonucleotide-primed PCR amplification of the tagged target nucleic acid sequences results in amplicons in which the reporter(s) is incorporated, thereby separating the reporter(s) from the quencher molecule(s). The resulting reporter signal(s) may be detected and are indicative of the presence of the corresponding allele in the sample.

Example 2

Tagging primers were designed for each polymorphic variant for various polymorphic sites. In addition to the target-specific sequences, the tagging primers were designed to contain a nucleotide tag sequences at the 5' end. When testing a polymorphic site, the tagging primers for the first alleles contained a different nucleotide tag sequence than the tagging primers for the second allele. The sequences of the primers containing both nucleotide tag sequences and the target-specific sequences are listed in Table 1.

Reverse primers were designed to flank the target polynucleotide and are listed in Table 2.

Multiple sets of probe oligonucleotide/regulatory oligonucleotide pairs were designed. The probe oligonucleotides contained a variety of nucleotide tag sequences at the 3' end corresponding to the nucleotide tag sequences on the tagging primers. The probe oligonucleotides contained regulatory sequences at the 3' end that were recognized by the corresponding regulatory oligonucleotide. The probe oligonucleotides were labeled with a fluorescent reporter molecule at the 3' end. The fluorescent dyes were selected from FAM, CalOrange, and HEX. The regulatory oligonucleotides were labeled with a corresponding quencher at the 5' end.

When testing a polymorphic site, two sets of probe oligonucleotide/regulatory oligonucleotide pairs were used. Each set contained a different reporter quencher pair and a different nucleotide tag sequence corresponding to the nucleotide tag sequences in the tagging primers.

The sequences of the probe oligonucleotide/regulatory oligonucleotide pairs are listed in Tables 3 and 4.

The oligonucleotides were synthesized by Operon at 10 nmol scale, and provided resuspended in TE buffer (Teknova) at a concentration of 100 uM.

Human genomic DNA samples from the Coriell sample collection were resuspended at 60 ng/μl in low-EDTA TE buffer (Teknova), and prepared for PCR as follows.

A Probe Mix was prepared as follows: Each probe oligonucleotide was prepared at 6 uM final concentration in DNA Suspension Buffer (10 mM Tris, pH 8.0, 0.1 mM EDTA, TEKnova, PN T0221) with 30 mM EDTA. Each regulatory oligonucleotide was prepared at 30 uM final concentration in the same buffer.

A Sample Mix was prepared as follows:
Biotium Fast Probe Master Mix (Biotium, PN 31005), 20X SNPtype SampleLoading Reagent (Fluidigm, PN 100-3425), Probe Mix, 50X ROX (Invitrogen, PN 12223-012) and PCR-certified water were combined to make the Sample Pre-Mix as described in Table 5. 2.5 μL of each genomic DNA (gDNA) sample at 60 ng/μl were added to 3.5 μL of Sample Pre-Mix to make a total of 6 μL of Sample Mix solution. The Sample Mix was vortexed for a minimum of 20 seconds, and then centrifuged for at least 30 seconds to spin down all components.

An Assay Mix was prepared as follows:
An Assay Mix containing two tagging primers, one for each allele, a corresponding reverse primer and DNA Suspension Buffer (10 mM Tris, pH 8.0, 0.1 mM EDTA, TEKnova, PN T0221) was prepared as described in Table 6 below.

10X Assays were prepared as follows:
Aliquots of 10X assays were prepared using volumes in Table 7 below in a DNA-free hood. The 2X Assay Loading Reagent (Fluidigm, PN 85000736) was combined with PCR-certified water to create the Assay Pre-Mix. 4 μL of the Assay Pre-Mix was combined with 1 μL of each individual Assay Pre-Mix Mix for a total of 5 μL 10X Assay Mix.

Running the 48.48 Dynamic Array™ IFC
The containment and interface accumulator reservoirs were filled with 300 μl of Control Line Fluid (Fluidigm PN 89000020. 5 μl of each Sample Mix was loaded into the sample inlets, and 4 μA of the appropriate 10X Assay Mix was loaded into each assay inlets on the 48.48 Dynamic Array™ IFC (Fluidigm, PN BMK-M-48.48).

The IFC was thermal cycled and imaged using an FC1™ Cycler manufactured by Fluidigm Corporation. The IFC thermal cycling protocol included a hotstart step [95° C. for 5 min], a 35 cycle touchdown PCR strategy [1 cycle of 95° C. for 15 sec, 64° C. for 45 sec, and 72° C. for 15 sec; 1 cycle of 95° C. for 15 sec, 63° C. for 45 sec, and 72° C. for 15 sec; 1 cycle of 95° C. for 15 sec, 62° C. for 45 sec, and 72° C. for 15 sec; 1 cycle of 95° C. for 15 sec, 61° C. for 45 sec, and 72° C. for 15 sec; and 34 cycles of 95° C. for 15 sec, 62° C. for 45 sec, and 72° C. for 15 sec], and a cooling step [1 cycle of 25° C. for 10 sec]. The data was collected in an EP1™ Reader manufactured by Fluidigm Corporation and analyzed using the SNP Genotyping Analysis Software v.3.1.0.

TABLE 1

Tagging Primers

| Tagging Primer Name | Reverse Primer Name | Tagging Primer Sequence | SEQ ID NO. |
|---|---|---|---|
| FASP_A_SNP3_ALA | FASP_SNP3_C2 | TGCGACTAAGAACGCTATCAGCCTAGGCATTGATTTTGAAGACATCAA | 1 |
| FASP_A_SNP3_ALG | FASP_SNP3_C2 | CAAGTGATCCGAGAGGTTGAACTAGGCATTGATTTTGAAGACATCAG | 2 |
| FASP_A_SNP6_ALC | FASP_SNP6_C1 | TGCGACTAAGAACGCTATCAGGCCATCATTTAGCTTTACACACTGG | 3 |
| FASP_A_SNP6_ALG | FASP_SNP6_C1 | CAAGTGATCCGAGAGGTTGAAGCCATCATTTAGCTTTACACACTGC | 4 |
| FASP_A_SNP8_ALA | FASP_SNP8_C1 | TGCGACTAAGAACGCTATCAGTTCCACAGTGTATGGCCTGTCA | 5 |
| FASP_A_SNP8_ALG | FASP_SNP8_C1 | CAAGTGATCCGAGAGGTTGAACCACAGTGTATGGCCTGTCG | 6 |
| FASP_B_SNP3_ALA | FASP_SNP3_C2 | GGTCACTGTCACGAGGGATATCCTAGGCATTGATTTTGAAGACATCAA | 7 |
| FASP_B_SNP6_ALC | FASP_SNP6_C1 | GGTCACTGTCACGAGGGATATGCCATCATTTAGCTTTACACACTGG | 8 |
| FASP_B_SNP8_ALA | FASP_SNP8_C1 | GGTCACTGTCACGAGGGATATTCCACAGTGTATGGCCTGTCA | 9 |
| FASP_B_SNP3_ALG | FASP_SNP3_C2 | GCTCCAACCTCTGACCTACTAACTAGGCATTGATTTTGAAGACATCAG | 10 |
| FASP_B_SNP6_ALG | FASP_SNP6_C1 | GCTCCAACCTCTGACCTACTAAGCCATCATTTAGCTTTACACACTGC | 11 |
| FASP_B_SNP8_ALG | FASP_SNP8_C1 | GCTCCAACCTCTGACCTACTAACCACAGTGTATGGCCTGTCG | 12 |
| FASP_3_SNP4_ALA | FASP_SNP4_C1 | GGTCACTGTCACGAGGGATATTTTCAAGTTCCTGACCTTCACATACT | 13 |
| FASP_4_SNP4_ALG | FASP_SNP4_C1 | GCTCCAACCTCTGACCTACTAACAAGTTCCTGACCTTCACATACC | 14 |
| FASP_3_SNP5_ALC | FASP_SNP5_C2 | GGTCACTGTCACGAGGGATATCACAGAAAGACATATTGGAAGTAACTTAC | 15 |
| FASP_4_SNP5_ALT | FASP_SNP5_C2 | GCTCCAACCTCTGACCTACTAACACAGAAAGACATATTGGAAGTAACTTAT | 16 |
| FASP_3_SNP6_ALC | FASP_SNP6_C1 | GGTCACTGTCACGAGGGATATGCCATCATTTAGCTTTACACACTGG | 8 |
| FASP_4_SNP6_ALG | FASP_SNP6_C1 | GCTCCAACCTCTGACCTACTAAGCCATCATTTAGCTTTACACACTGC | 11 |
| FASP_31_AY841151_ALG | FASP_31_AY841151_C | GGTCACTGTCACGAGGGATATCACAGTTGATTAATGATAGCAGAAC | 17 |
| FASP_31_AY841151_ALT | FASP_31_AY841151_C | GCTCCAACCTCTGACCTACTAACCTCACAGTTGATTAATGATAGCAGAAA | 18 |
| FASP_35_DQ422949_ALA | FASP_35_DQ422949_C | GGTCACTGTCACGAGGGATATCATAAACAAATGCCTTGTGGGGATCT | 19 |
| FASP_35_DQ422949_ALG | FASP_35_DQ422949_C | GCTCCAACCTCTGACCTACTAAATAAACAAATGCCTTGTGGGGATCC | 20 |
| FASP_55_DQ489377_ALC | FASP_55_DQ489377_C | GGTCACTGTCACGAGGGATATATTGAACCTTTAGTTGTGGTTTGTC | 21 |
| FASP_55_DQ489377_ALT | FASP_55_DQ489377_C | GCTCCAACCTCTGACCTACTAAGAACCTTTAGTTGTGGTTTGTT | 22 |
| FASP_9_DQ404150_ALC | FASP_9_DQ404150_C | GCTCCAACCTCTGACCTACTAAAGGCATAGGAGACAATTAGGAAGC | 23 |
| FASP_9_DQ404150_ALA | FASP_9_DQ404150_C | GGTCACTGTCACGAGGGATATCAAAGGCATAGGAGACAATTAGGAAGA | 24 |
| FASP_19_AY863214_ALG | FASP_19_AY863214_C | GCTCCAACCTCTGACCTACTAACCTTCCTCTCTTGGGACCG | 25 |
| FASP_19_AY863214_ALA | FASP_19_AY863214_C | GGTCACTGTCACGAGGGATATCCTTCCTCTCTTGGGACCA | 26 |
| FASP_55_DQ489377_ALT | FASP_55_DQ489377_C | GCTCCAACCTCTGACCTACTAAGAACCTTTAGTTGTGGTTTGTT | 22 |
| FASP_55_DQ489377_ALC | FASP_55_DQ489377_C | GGTCACTGTCACGAGGGATATATTGAACCTTTAGTTGTGGTTTGTC | 21 |
| FASP_31_AY841151_ALG | FASP_31_AY841151_C | GGTCACTGTCACGAGGGATATCACAGTTGATTAATGATAGCAGAAC | 17 |
| FASP_31_AY841151_ALT | FASP_31_AY841151_C | GCTCCAACCTCTGACCTACTAACCTCACAGTTGATTAATGATAGCAGAAA | 18 |
| FASP_35_DQ422949_ALA | FASP_35_DQ422949_C | GGTCACTGTCACGAGGGATATCATAAACAAATGCCTTGTGGGGATCT | 19 |
| FASP_35_DQ422949_ALG | FASP_35_DQ422949_C | GCTCCAACCTCTGACCTACTAAATAAACAAATGCCTTGTGGGGATCC | 20 |
| FASP_1_DQ381153_ALA | FASP_1_DQ381153_C | GGTCACTGTCACGAGGGATATGGACCTGGCCAGGCATTAA | 27 |
| FASP_1_DQ381153_ALC | FASP_1_DQ381153_C | GCTCCAACCTCTGACCTACTAAGACCTGGCCAGGCATTAC | 28 |
| FASP_65_AY853302_ALA | FASP_65_AY853302_C | GGTCACTGTCACGAGGGATATGCAAATAATTTATAGAGAACCTAGTGTGAAT | 29 |
| FASP_65_AY853302_ALG | FASP_65_AY853302_C | GCTCCAACCTCTGACCTACTAACAAATAATTTATAGAGAACCTAGTGTGAAC | 30 |

TABLE 1-continued

Tagging Primers

| Tagging Primer Name | Reverse Primer Name | Tagging Primer Sequence | SEQ ID NO. |
|---|---|---|---|
| FASP_72_AY929334_ALC | FASP_72_AY929334_C | GGTCACTGTCACGAGGGATATCCTGGGAAAGAAAAGGGTTGAG | 31 |
| FASP_72_AY929334_ALT | FASP_72_AY929334_C | GCTCCAACCTCTGACCTACTAACTCCTGGGAAAGAAAAGGGTTGAA | 32 |
| FASP_AA_52_DQ435443_ALA | FASP_AA_52_DQ435443_C | TGCGACTAAGAACGCTATCAGGTAGCAGAAGGCGAAATAATTCATAATTA | 33 |
| FASP_AA_52_DQ435443_ALC | FASP_AA_52_DQ435443_C | CAAGTGATCCGAGAGGTTGAAGTAGCAGAAGGCGAAATAATTCATAATTC | 34 |
| FASP_AA_61_AY842475_ALA | FASP_AA_61_AY842475_C | TGCGACTAAGAACGCTATCAGCATCTCTAAGCTGTATGTGTGAGCA | 35 |
| FASP_AA_61_AY842475_ALG | FASP_AA_61_AY842475_C | CAAGTGATCCGAGAGGTTGAAATCTCTAAGCTGTATGTGTGAGCG | 36 |

TABLE 2

Reverse Primers

| Reverse Primer Name | Tagging Primer Names | Reverse Primer Sequence | SEQ ID NO. |
|---|---|---|---|
| FASP_SNP3_C2 | FASP_A_SNP3_ALA<br>FASP_A_SNP3_ALG<br>FASP_B_SNP3_ALA<br>FASP_B_SNP3_ALG | GTCTCTGAAGTCAACCTCACCAGAA | 37 |
| FASP_SNP6_C1 | FASP_A_SNP6_ALC<br>FASP_A_SNP6_ALG<br>FASP_B_SNP6_ALC<br>FASP_B_SNP6_ALG<br>FASP_3_SNP6_ALC<br>FASP_4_SNP6_ALG | GCTAGTCAGACAAGTGACAGGGAAT | 38 |
| FASP_SNP8_C1 | FASP_A_SNP8_ALA<br>FASP_A_SNP8_ALG<br>FASP_B_SNP8_ALA<br>FASP_B_SNP8_ALG | TTGTGCACCCACACTGGGAGCT | 39 |
| FASP_SNP4_C1 | FASP_3_SNP4_ALA<br>FASP_4_SNP4_ALG | GTATAGCTTGCCAAAAGTAGGTACTTCAA | 40 |
| FASP_SNP5_C2 | FASP_3_SNP5_ALC<br>FASP_4_SNP5_ALT | GCACTCAGAAAACTCACTGAAAGGTTATT | 41 |
| FASP_31_AY841151_C | FASP_31_AY841151_ALG<br>FASP_31_AY841151_ALT | TTGCCTTCCAAAGATGGTTCATGGAATT | 42 |
| FASP_35_DQ422949_C | FASP_35_DQ422949_ALA<br>FASP_35_DQ422949_ALG | CCTGAAGGAATATCCACCCTGCAAA | 43 |
| FASP_55_DQ489377_C | FASP_55_DQ489377_ALC<br>FASP_55_DQ489377_ALT | AGAAGGAAAAGTGGCAGAGTTTGGAAAT | 44 |
| FASP_9_DQ404150_C | FASP_9_DQ404150_ALC<br>FASP_9_DQ404150_ALA | ACTGCTTAAAGTTCTAAACCAATCAACAAT | 45 |
| FASP_19_AY863214_C | FASP_19_AY863214_ALG<br>FASP_19_AY863214_ALA | AGGATGAAGTGGCAGGGAC | 46 |
| FASP_55_DQ489377_C | FASP_55_DQ489377_ALT<br>FASP_55_DQ489377_ALC | AGAAGGAAAAGTGGCAGAGTTTGGAAAT | 44 |
| FASP_31_AY841151_C | FASP_31_AY841151_ALG<br>FASP_31_AY841151_ALT | TTGCCTTCCAAAGATGGTTCATGGAATT | 42 |
| FASP_35_DQ422949_C | FASP_35_DQ422949_ALA<br>FASP_35_DQ422949_ALG | CCTGAAGGAATATCCACCCTGCAAA | 43 |
| FASP_1_DQ381153_C | FASP_1_DQ381153_ALA<br>FASP_1_DQ381153_ALC | CAAGCTCCCAAGGGCATCTC | 47 |
| FASP_65_AY853302_C | FASP_65_AY853302_ALA<br>FASP_65_AY853302_ALG | GCTTCCTGTATTCCCTTTGTTGTCTAAT | 48 |

TABLE 2-continued

| Reverse Primers | | | |
|---|---|---|---|
| Reverse Primer Name | Tagging Primer Names | Reverse Primer Sequence | SEQ ID NO. |
| FASP_72_AY929334_C | FASP_72_AY929334_ALC<br>FASP_72_AY929334_ALT | GCCCCACTCTCAAAATCTGAGACTT | 49 |
| FASP_AA_52_DQ435443_C | FASP_AA_52_DQ435443_ALA<br>FASP_AA_52_DQ435443_ALC | CTATCTAGTGGTCACCAACCTAGCTA | 50 |
| FASP_AA_61_AY842475_C | FASP_AA_61_AY842475_ALA<br>FASP_AA_61_AY842475_ALG | GATACATCCTCTTACCTAATCTGAGCTTT | 51 |

TABLE 3

| Probe oligonucleotides ("Probe oligonucleotides") | | | | |
|---|---|---|---|---|
| Probe oligonucleotide Oligonucleotide Name | Regulatory oligonucleotide Names | Tagging Primer Names With Recognized Tags | Probe oligonucleotide Sequence | SEQ ID NO. |
| FASP_A_F2_FAM | FASP_A_Q2<br>FASP_A_Q2.2<br>FASP_A_Q1 | FASP_A_SNP3_ALA<br>FASP_A_SNP6_ALC<br>FASP_A_SNP8_ALA<br>FASP_AA_19_AY863214_ALA<br>FASP_AA_52_DQ435443_ALA<br>FASP_AA_61_AY842475_ALA | CCAGAATCATCGTGGATGCGACTAAGAACGCTATCAG | 52 |
| FASP_A_F1_CalOrange | FASP_A_Q1 | FASP_A_SNP3_ALG<br>FASP_A_SNP6_ALG<br>FASP_A_SNP8_ALG | TAGGTCGAGGGATCTTCAAGTGATCCGAGAGGTTGAA | 53 |
| FASP_B_F3_FAM | FASP_B_Q3<br>FASP_B_Q3.1<br>FASP_B_Q3.2<br>FASP_B_Q3.3<br>FASAP_B_Q3.2_TIDE2 | FASP_B_SNP3_ALA<br>FASP_B_SNP6_ALC<br>FASP_B_SNP8_ALA<br>FASP_3_SNP4_ALA<br>FASP_3_SNP5_ALC<br>FASP_3_SNP6_ALC<br>FASP_1_DQ381153_ALA<br>FASP_65_AY853302_ALA<br>FASP_72_AY929334_ALC | GTAGCACAACTCGCAGGTCACTGTCACGAGGGATAT | 54 |
| FASP_B_F4_CalOrange | FASP_B_Q3<br>FASP_B_Q4.1<br>FASP_B_Q4.2<br>FASP_B_Q4.3 | FASP_B_SNP3_ALG<br>FASP_B_SNP6_ALG<br>FASP_B_SNP8_ALG<br>FASP_4_SNP4_ALG<br>FASP_4_SNP5_ALT<br>FASP_4_SNP6_ALG<br>FASP_31_AY841151_ALT<br>FASP_35_DQ422949_ALG<br>FASP_55_DQ489377_ALT | GTATGGTTTCCCGCTGCTCCAACCTCTGACCTACTAA | 55 |
| FASP_B_F3_FAM_A | FASP_B_Q3.2_A<br>FASP_B_Q5 | FASP_31_AY841151_ALG<br>FASP_35_DQ422949_ALA<br>FASP_55_DQ489377_ALC | ATAGCACAACTCGCAGGTCACTGTCACGAGGGATAT | 56 |
| FASP_B_F3_FAM_swap | FASP_B_Q3.2 | FASP_9_DQ404150_ALC<br>FASP_19_AY863214_ALG<br>FASP_55_DQ489377_ALT | GTAGCACAACTCGCAGCTCCAACCTCTGACCTACTAA | 57 |
| FASP_B_F4_CalOrange_swap | FASP_B_Q4.2 | FASP_9_DQ404150_ALA<br>FASP_19_AY863214_ALA<br>FASP_55_DQ489377_ALC | GTATGGTTTCCCGCTGGTCACTGTCACGAGGGATAT | 58 |
| FASP_B_F4_HEX | FASP_B_Q4.2_TIDE3 | FASP_1_DQ381153_ALC<br>FASP_65_AY853302_ALG<br>FASP_72_AY929334_ALT | GTATGGTTTCCCGCTGCTCCAACCTCTGACCTACTAA | 55 |
| FASP_A_F1_HEX | FASP_A_Q1.2 | FASP_AA_19_AY863214_ALG<br>FASP_AA_52_DQ435443_ALC<br>FASP_AA_61_AY842475_ALG | TAGGTCGAGGGATCTTCAAGTGATCCGAGAGGTTGAA | 53 |

TABLE 4

Regulatory oligonucleotides

| Regulatory oligonucleotide Name | Probe oligonucleotide Names | Regulatory oligonucleotide Sequence | SEQ ID NO. |
|---|---|---|---|
| FASP_A_Q2 | FASP_A_F2_FAM | TCCACGATGATTCTGG | 59 |
| FASP_A_Q1 | FASP_A_F1_CalOrange | AAGATCCCTCGACCTA | 60 |
| FASP_B_Q3 | FASP_B_F3_FAM | TGCGAGTTGTGCTAC | 61 |
| FASP_B_Q4 | FASP_B_F4_CalOrange | AGCGGGAAACCATAC | 62 |
| FASP_B_Q3.1 | FASP_B_F3_FAM | GACCTGCGAGTTGTGCTAC | 63 |
| FASP_B_Q4.1 | FASP_B_F4_CalOrange | GAGCAGCGGGAAACCATAC | 65 |
| FASP_B_Q3.2 | FASP_B_F3_FAM<br>FASP_B_F3_FAM_swap | CCGGTGCGAGTTGTGCTAC | 65 |
| FASP_B_Q4.2 | FASP_B_F4_CalOrange<br>FASP_B_F4_CalOrange_swap | CCCGAGCGGGAAACCATAC | 66 |
| FASP_B_Q3.3 | FASP_B_F3_FAM | GCTGCGGGTTGTGCTGCC | 67 |
| FASP_B_Q4.3 | FASP_B_F4_CalOrange | CCGGCGGGAAACCGTGC | 68 |
| FASP_B_Q3.2_A | FASP_B_F3_FAM_A | CCGGTGCGAGTTGTGCTAT | 69 |
| FASP_BQ5 | FASP_B_F3_FAM_A | TGCGAGTTGTGCTATGGGG | 70 |
| FASP_B_Q3.2_TIDE2 | FASP_B_F3_FAM | CCGGTGCGAGTTGTGCTAC | 65 |
| FASP_B_Q4.2_TIDE3 | FASP_B_F4_HEX | CCCGAGCGGGAAACCATAC | 66 |
| FASP_A_Q2.2 | FASP_A_F2_FAM | GCGGTCCACGATGATTCTGG | 71 |
| FASP_A_Q1.2 | FASP_A_F1_HEX | GCCCAAGATCCCTCGACCTA | 72 |

TABLE 5

Sample Pre-Mix

| Component | Volume per Inlet (uL) |
|---|---|
| Biotium 2X Fast Probe Master Mix | 3.0 |
| 20X SNPtype SampleLoading Reagent | 0.3 |
| Probe Mix | 0.1 |
| 50X ROX | 0.036 |
| PCR-certified water | 0.064 |
| Total | 3.5 |

TABLE 6

Assay Mix

| Component | Volume (uL) |
|---|---|
| Tagging Primers (100 uM each) | 3.0 |
| Reverse Primer | 8.0 |
| DNA Suspension Buffer | 29.0 |
| Total | 40.0 |

TABLE 7

10X Assays

| Component | Volume per Inlet (uL) |
|---|---|
| 2X Assay Loading Reagent | 2.5 |
| PCR-certified water | 1.5 |
| Assay Mix | 1.0 |
| Total | 5.0 |

For illustration and not limitation, the following exemplary embodiments are also contemplated:

Embodiment 1. A method of detecting a polynucleotide with a target nucleotide sequence comprising: tagging the polynucleotide comprising a desired target nucleotide sequence with a nucleotide tag; providing a probe oligonucleotide with a melting temperature Tm1, comprising a regulatory sequence and a nucleotide tag recognition sequence; incorporating the probe oligonucleotide into the tagged polynucleotide in a polynucleotide amplification reaction; providing a regulatory oligonucleotide with a melting temperature Tm2, comprising a sequence segment that is at least partially complementary to the regulatory sequence; wherein Tm1 and Tm2 are higher than the annealing temperature associated with the polynucleotide amplification reaction and the signal associated with the probe oligonucleotide is dependent on its rescue from the regulatory nucleotide.

Embodiment 2. The method of embodiment 1, wherein the polynucleotide amplification reaction is PCR.

Embodiment 3. The method of embodiment 1, wherein the probe oligonucleotide and the regulatory oligonucleotide are labeled at complementary sites.

Embodiment 4. The method of embodiment 1, wherein a plurality of target nucleotide sequences is assayed within a single reaction by tagging each polynucleotide comprising one of the desired target nucleotide sequences with a different nucleotide tag encoding the target nucleotide sequence; providing at least one probe oligonucleotide, wherein the nucleotide tag recognition sequence preferentially hybridizes to one of the nucleotide tags; and providing at least one regulatory oligonucleotide, wherein a portion of the regulatory oligonucleotide preferentially hybridizes to one of the regulatory sequences.

Embodiment 5. The method of embodiment 4, wherein the relative abundance of the target nucleotide sequences are determined.

Embodiment 6. The method of embodiment 1, wherein the polynucleotide is tagged by elongating from a tagging primer.

Embodiment 7. The method of embodiment 1 or 6, wherein the target polynucleotide sequence(s) comprises at least one polymorphic site.

Embodiment 8. The method of embodiment 7, wherein the polymorphic site is located within the target nucleotide sequence.

Embodiment 9. The method of embodiment 7, wherein the polymorphism comprises a point mutation.

Embodiment 10. The method of embodiment 7, wherein the polymorphism comprises an insertion.

Embodiment 11. The method of embodiment 7, wherein the polymorphism comprises a deletion.

Embodiment 12. The method of embodiment 10 or 11, wherein the polymorphism spans more than one nucleotide.

Embodiment 13. The method of embodiment 1, wherein when the regulatory oligonucleotide is aligned with the regulatory sequence on the probe oligonucleotide, the regulatory oligonucleotide comprises a completely uncomplementary auxiliary sequence segment.

Embodiment 14. The method of embodiment 13, wherein the auxiliary sequence segment at least partially overlaps with the probe oligonucleotide.

Embodiment 15. The method of embodiment 14, wherein the auxiliary sequence segment at least partially overlaps with the nucleotide tag recognition sequence.

Embodiment 16. The method of embodiment 1 or 2, wherein the signal is detected over time.

Embodiment 17. The method of embodiment 1 or 16, wherein the temperature is adjusted facilitating the hybridization of the unincorporated probe oligonucleotide to the regulatory oligonucleotide, such that the ratio of the unhybridized unincorporated probe oligonucleotide to the incorporated probe oligonucleotide is less than 1.

Embodiment 18. The method of embodiment 17, wherein the ratio of the unhybridized unincorporated probe oligonucleotide to the incorporated probe oligonucleotide is less than 0.5.

Embodiment 19. The method of embodiment 17, wherein the ratio of the unhybridized unincorporated probe oligonucleotide to the incorporated probe oligonucleotide is less than 0.2.

Embodiment 20. The method of embodiment 17, wherein the ratio of the unhybridized unincorporated probe oligonucleotide to the incorporated probe oligonucleotide is less than 0.1.

Embodiment 21. The method of embodiment 17, wherein the ratio of the unhybridized unincorporated probe oligonucleotide to the incorporated probe oligonucleotide is less than 0.05.

Embodiment 22. The method of embodiment 17, wherein the ratio of the unhybridized unincorporated probe oligonucleotide to the incorporated probe oligonucleotide is less than 0.02.

Embodiment 23. The method of embodiment 17, wherein the ratio of the unhybridized unincorporated probe oligonucleotide to the incorporated probe oligonucleotide is less than 0.01.

Embodiment 24. The method of embodiment 17, wherein the ratio of the unhybridized unincorporated probe oligonucleotide to the incorporated probe oligonucleotide is less than 0.005.

Embodiment 25. The method of embodiment 1 or 2, wherein at least a portion of the assay is conducted in droplets.

Embodiment 26. The method of any one of embodiments 1, 2, or 16-24, wherein the regulatory oligonucleotides are attached to supports.

Embodiment 27. The method of embodiment 26, wherein the supports are beads.

Embodiment 28. The method of embodiment 27, wherein the beads are magnetic.

Embodiment 29. The method of embodiment 27 or 28, wherein the supports are diverted out of the region where the signal is detected.

Embodiment 30. The method of embodiment 1, wherein one of the probe oligonucleotide and regulatory oligonucleotide is labeled with a reporter molecule and the other with a quencher molecule of a reporter-quencher pair, wherein the quencher is capped providing protection from nucleases.

Embodiment 31. The method of embodiment 30, wherein the capping is at the 3' end.

Embodiment 32. The method of embodiment 6, wherein the polymorphic site(s) is predictive of a genetic trait.

Embodiment 33. The method of embodiment 6, wherein the polymorphic site(s) is predictive of a disease risk.

Embodiment 34. The method of embodiment 6, wherein the polymorphic site(s) is predictive of a carrier status for a disease.

Embodiment 35. The method of embodiment 6, wherein the polymorphic site(s) is predictive of a carrier status for a genetic trait.

Embodiment 36. The method of embodiment 6, wherein the polymorphic site(s) is predictive of a response to drug treatment.

Embodiment 37. The method of embodiment 37, wherein the response to drug treatment is selected from the group consisting of Abacavir Hypersensitivity, Risk of Esophageal Cancer in response to alcohol consumption and smoking, Antidepressant Response, Beta-Blocker Response, Caffeine Metabolism, Clopidogrel (Plavix®) Efficacy, Floxacillin Toxicity, Fluorouracil Toxicity, Heroin Addiction, Lumiracoxib (Prexige®) Side Effects, Metformin Response, Naltrexone Treatment Response, Risk of Venous Thromboembolism in response to oral contraceptives and hormone replacement therapy, Postoperative Nausea and Vomiting (PONV), Pseudocholinesterase Deficiency, Response to Hepatitis C Treatment, Response to Interferon Beta Therapy, Statin Response, and Warfarin (Coumadin®) Sensitivity.

Embodiment 38. The method of embodiment 1 or 4, wherein the polynucleotide sequence(s) is predictive of a phylogenetic domain.

Embodiment 39. The method of embodiment 1 or 4, wherein the polynucleotide sequence(s) is predictive of a phylogenetic kingdom.

Embodiment 40. The method of embodiment 1 or 4, wherein the polynucleotide sequence(s) is predictive of a phylogenetic phylum.

Embodiment 41. The method of embodiment 1 or 4, wherein the polynucleotide sequence(s) is predictive of a phylogenetic class.

Embodiment 42. The method of embodiment 1 or 4, wherein the polynucleotide sequence(s) is predictive of a phylogenetic order.

Embodiment 43. The method of embodiment 1 or 4, wherein the polynucleotide sequence(s) is predictive of a phylogenetic family.

Embodiment 44. The method of embodiment 1 or 4, wherein the polynucleotide sequence(s) is predictive of a phylogenetic genus.

Embodiment 45. The method of embodiment 1 or 4, wherein the polynucleotide sequence(s) is predictive of a phylogenetic species.

Embodiment 46. A polynucleotide detection reagent for detecting a target polynucleotide comprising: an probe oligonucleotide with a melting temperature Tm1, comprising a regulatory sequence and a nucleotide tag recognition sequence; and a regulatory oligonucleotide with a melting temperature Tm2, comprising a sequence segment that is at least partially complementary to the regulatory sequence; wherein Tm1 and Tm2 are higher than a yielding annealing temperature associated with a reaction amplifying the polynucleotide and the signal associated with the probe oligonucleotide is dependent on its rescue from the regulatory nucleotide.

Embodiment 47. The reagent of embodiment 46, wherein the reaction amplifying the polynucleotide is PCR.

Embodiment 48. The reagent of embodiment 46, wherein the probe oligonucleotide and the regulatory oligonucleotide are labeled at complementary sites.

Embodiment 49. The reagent of embodiment 46, for detecting a plurality of polynucleotides, further comprising a plurality of probe oligonucleotides, with different nucleotide tag recognition sequences identifiably paired with different regulatory sequences; and a plurality of regulatory oligonucleotides, wherein a portion of the regulatory oligonucleotides preferentially hybridizes to one of the regulatory sequences.

Embodiment 50. The reagent of embodiment 49, wherein the nucleotide tag recognition sequences preferentially hybridize with a nucleotide tag encoding a target nucleotide sequence on a target polynucleotide.

Embodiment 51. The reagent of embodiment 50, wherein the relative abundance of the target nucleotide sequences are determined.

Embodiment 52. The reagent of embodiment 46 or 49, wherein the target polynucleotide sequence(s) comprises at least one polymorphic site.

Embodiment 53. The reagent of embodiment 46, wherein the polymorphic site is located within the target nucleotide sequence.

Embodiment 54. The reagent of embodiment 52, wherein the polymorphism comprises a point mutation.

Embodiment 55. The reagent of embodiment 52, wherein the polymorphism comprises an insertion.

Embodiment 56. The reagent of embodiment 52, wherein the polymorphism comprises a deletion.

Embodiment 57. The reagent of embodiment 55 or 56, wherein the polymorphism spans more than one nucleotide.

Embodiment 58. The reagent of embodiment 46, wherein when the regulatory oligonucleotide is aligned with the regulatory sequence on the probe oligonucleotide, the regulatory oligonucleotide comprises a completely uncomplementary auxiliary sequence segment.

Embodiment 59. The reagent of embodiment 46 or 47, wherein the signal is detected Embodiment 60. A system for detecting a target polynucleotide with a target nucleotide sequence comprising: an probe oligonucleotide, comprising a regulatory sequence and a nucleotide tag recognition sequence, with a melting temperature Tm1; a regulatory oligonucleotide, comprising a sequence segment that is at least partially complementary to the regulatory sequence, with a melting temperature Tm2; wherein Tm1 and Tm2 are higher than a yielding annealing temperature associated with a reaction amplifying the polynucleotide, wherein the probe oligonucleotide is incorporated into the polynucleotide in a polynucleotide amplification reaction, and wherein the signal associated with the probe oligonucleotide is dependent on its rescue from the regulatory nucleotide; and a detector operably disposed to acquire the signal associated with the probe oligonucleotide.

Embodiment 61. The system of embodiment 60, wherein the polynucleotide amplification reaction is performed by thermal cycling.

Embodiment 62. The system of embodiment 61, wherein a thermal cycler is operably disposed to thermally cycle the contents of the reaction.

Embodiment 63. The system of embodiment 60, wherein reagents for an amplification reaction are provided.

It is understood that the invention is not limited to the particular methodology, protocols, and reagents, etc., described herein, as these can be varied by the skilled artisan. It is also understood that the terminology used herein is used for the purpose of describing particular illustrative embodiments only, and is not intended to limit the scope of the invention. The embodiments of the invention and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the invention.

We claim:

1. A method for detecting a target nucleotide sequence comprising:

a) tagging the target nucleotide sequence with a nucleotide tag sequence, thereby producing a tagged target nucleic acid sequence;

b) providing a probe oligonucleotide comprising a nucleotide tag recognition sequence complementary to the nucleotide tag sequence and a regulatory sequence 5' to the nucleotide tag recognition sequence, wherein said probe oligonucleotide comprises a first label and has a melting temperature Tm1;

c) amplifying the tagged target nucleic acid sequence in a PCR amplification reaction using the probe oligonucleotide as a primer, wherein said PCR amplification reaction is characterized by an annealing temperature Ta;

wherein the PCR amplification reaction is carried out in the presence of a regulatory oligonucleotide comprising a sequence segment that is complementary to the regulatory sequence, wherein said regulatory oligonucleotide comprises a second label and has a melting temperature Tm2; and d) detecting the product of the PCR amplification reaction; wherein the first label and the second label constitute a fluorescent reporter/quencher pair; and wherein Tm1 and Tm2 are both higher than Ta.

2. The method of claim 1 wherein the nucleotide tag sequence is incorporated into the tagged target nucleic acid sequence using a PCR reaction.

3. The method of claim 1 wherein the nucleotide tag recognition sequence is exactly complementary to the nucleotide tag sequence.

4. The method of claim 1 wherein the regulatory oligonucleotide comprises a sequence segment that is exactly complementary to the regulatory sequence.

5. The method of claim 4 wherein the regulatory oligonucleotide has a length in the range of 15-45 nucleotides.

6. The method of claim 1 wherein Ta is in the range of 55-62° C.

7. The method of claim 1 wherein Ta is in the range of 60-64° C.

8. The method of claim 1 wherein Ta is in the range of 60° C.-62° C.

9. The method of claim 1 wherein Tm1 is at least 25° C. higher than the annealing temperature (Ta).

10. The method of claim 9 wherein Tm2 is at least 2° C. higher than the annealing temperature (Ta).

11. The method of claim 10 wherein Tm2 is in the range of 60-75° C.

12. The method of claim 8 wherein the PCR amplification reaction is carried out in a reaction volume greater than 500 nL.

13. The method of claim 12 wherein the PCR amplification reactions are carried out in a multiwell plate comprising 96-1536 wells.

14. The method of claim 8 wherein the PCR amplification reaction is carried out in a reaction volume less than 100 nL.

15. The method of claim 14 wherein the PCR amplification reaction is carried out in a microfluidic device.

16. The method of claim 14 wherein Ta is 60° C.

17. The method of claim 8 wherein the PCR amplification reaction comprises at least 20 cycles at the annealing temperature (Ta).

18. The method of claim 9 wherein Tm2 is at least 4° C. higher than the annealing temperature (Ta).

19. The method of claim 9 wherein Tm2 is at least 10° C. higher than the annealing temperature (Ta).

20. The method of claim 8 wherein the PCR amplification reaction is carried out in a reaction volume greater than 1 uL.

* * * * *

SEQUENCE LISTING

<160> NUMBER OF SEQ ID NOS: 72

<210> SEQ ID NO 1
<211> LENGTH: 48
<212> TYPE: DNA
<213> ORGANISM: Artificial sequence
<220> FEATURE:
<223> OTHER INFORMATION: Synthetic DNA -continued

<400> SEQUENCE: 1
tgcgactaag aacgctatca gcctaggcat tgattttgaa gacatcaa         48

<210> SEQ ID NO 2
<211> LENGTH: 47
<212> TYPE: DNA
<213> ORGANISM: Artificial sequence
<220> FEATURE:
<223> OTHER INFORMATION: Synthetic DNA

<400> SEQUENCE: 2
caagtgatcc gagaggttga actaggcatt gattttgaag acatcag          47

<210> SEQ ID NO 3
<211> LENGTH: 46
<212> TYPE: DNA
<213> ORGANISM: Artificial sequence
<220> FEATURE:
<223> OTHER INFORMATION: Synthetic DNA

<400> SEQUENCE: 3
tgcgactaag aacgctatca ggccatcatt tagctttaca cactgg           46

<210> SEQ ID NO 4
<211> LENGTH: 46
<212> TYPE: DNA
<213> ORGANISM: Artificial sequence
<220> FEATURE:
<223> OTHER INFORMATION: Synthetic DNA

<400> SEQUENCE: 4
caagtgatcc gagaggttga agccatcatt tagctttaca cactgc           46

<210> SEQ ID NO 5
<211> LENGTH: 43
<212> TYPE: DNA
<213> ORGANISM: Artificial sequence
<220> FEATURE:
<223> OTHER INFORMATION: Synthetic DNA

<400> SEQUENCE: 5
tgcgactaag aacgctatca gttccacagt gtatggcctg tca              43

<210> SEQ ID NO 6
<211> LENGTH: 41
<212> TYPE: DNA
<213> ORGANISM: Artificial sequence
<220> FEATURE:
<223> OTHER INFORMATION: Synthetic DNA

<400> SEQUENCE: 6
caagtgatcc gagaggttga accacagtgt atggcctgtc g                41

<210> SEQ ID NO 7
<211> LENGTH: 48
<212> TYPE: DNA
<213> ORGANISM: Artificial sequence
<220> FEATURE:
<223> OTHER INFORMATION: Synthetic DNA

<400> SEQUENCE: 7
ggtcactgtc acgagggata tcctaggcat tgattttgaa gacatcaa         48

<210> SEQ ID NO 8

<211> LENGTH: 46
<212> TYPE: DNA
<213> ORGANISM: Artificial sequence
<220> FEATURE:
<223> OTHER INFORMATION: Synthetic DNA

<400> SEQUENCE: 8
ggtcactgtc acgagggata tgccatcatt tagctttaca cactgg        46

<210> SEQ ID NO 9
<211> LENGTH: 43
<212> TYPE: DNA
<213> ORGANISM: Artificial sequence
<220> FEATURE:
<223> OTHER INFORMATION: Synthetic DNA

<400> SEQUENCE: 9
ggtcactgtc acgagggata tttccacagt gtatggcctg tca        43

<210> SEQ ID NO 10
<211> LENGTH: 48
<212> TYPE: DNA
<213> ORGANISM: Artificial sequence
<220> FEATURE:
<223> OTHER INFORMATION: Synthetic DNA

<400> SEQUENCE: 10
gctccaacct ctgacctact aactaggcat tgattttgaa gacatcag        48

<210> SEQ ID NO 11
<211> LENGTH: 47
<212> TYPE: DNA
<213> ORGANISM: Artificial sequence
<220> FEATURE:
<223> OTHER INFORMATION: Synthetic DNA

<400> SEQUENCE: 11
gctccaacct ctgacctact aagccatcat ttagctttac acactgc        47

<210> SEQ ID NO 12
<211> LENGTH: 42
<212> TYPE: DNA
<213> ORGANISM: Artificial sequence
<220> FEATURE:
<223> OTHER INFORMATION: Synthetic DNA

<400> SEQUENCE: 12
gctccaacct ctgacctact aaccacagtg tatggcctgt cg        42

<210> SEQ ID NO 13
<211> LENGTH: 47
<212> TYPE: DNA
<213> ORGANISM: Artificial sequence
<220> FEATURE:
<223> OTHER INFORMATION: Synthetic DNA

<400> SEQUENCE: 13
ggtcactgtc acgagggata ttttcaagtt cctgaccttc acatact        47

<210> SEQ ID NO 14
<211> LENGTH: 45
<212> TYPE: DNA
<213> ORGANISM: Artificial sequence
<220> FEATURE:
<223> OTHER INFORMATION: Synthetic DNA

<400> SEQUENCE: 14

```
gctccaacct ctgacctact aacaagttcc tgaccttcac atacc          45

<210> SEQ ID NO 15
<211> LENGTH: 50
<212> TYPE: DNA
<213> ORGANISM: Artificial sequence
<220> FEATURE:
<223> OTHER INFORMATION: Synthetic DNA

<400> SEQUENCE: 15
ggtcactgtc acgagggata tcacagaaag acatattgga agtaacttac    50

<210> SEQ ID NO 16
<211> LENGTH: 51
<212> TYPE: DNA
<213> ORGANISM: Artificial sequence
<220> FEATURE:
<223> OTHER INFORMATION: Synthetic DNA

<400> SEQUENCE: 16
gctccaacct ctgacctact aacacagaaa gacatattgg aagtaactta t  51

<210> SEQ ID NO 17
<211> LENGTH: 46
<212> TYPE: DNA
<213> ORGANISM: Artificial sequence
<220> FEATURE:
<223> OTHER INFORMATION: Synthetic DNA

<400> SEQUENCE: 17
ggtcactgtc acgagggata tcacagttga ttaatgatag cagaac        46

<210> SEQ ID NO 18
<211> LENGTH: 50
<212> TYPE: DNA
<213> ORGANISM: Artificial sequence
<220> FEATURE:
<223> OTHER INFORMATION: Synthetic DNA

<400> SEQUENCE: 18
gctccaacct ctgacctact aacctcacag ttgattaatg atagcagaaa    50

<210> SEQ ID NO 19
<211> LENGTH: 47
<212> TYPE: DNA
<213> ORGANISM: Artificial sequence
<220> FEATURE:
<223> OTHER INFORMATION: Synthetic DNA

<400> SEQUENCE: 19
ggtcactgtc acgagggata tcataaacaa atgccttgtg gggatct       47

<210> SEQ ID NO 20
<211> LENGTH: 47
<212> TYPE: DNA
<213> ORGANISM: Artificial sequence
<220> FEATURE:
<223> OTHER INFORMATION: Synthetic DNA

<400> SEQUENCE: 20
gctccaacct ctgacctact aaataaacaa atgccttgtg gggatcc       47

<210> SEQ ID NO 21
<211> LENGTH: 46
<212> TYPE: DNA
```

<213> ORGANISM: Artificial sequence
<220> FEATURE:
<223> OTHER INFORMATION: Synthetic DNA

<400> SEQUENCE: 21
ggtcactgtc acgagggata tattgaacct ttagttgtgg tttgtc            46

<210> SEQ ID NO 22
<211> LENGTH: 44
<212> TYPE: DNA
<213> ORGANISM: Artificial sequence
<220> FEATURE:
<223> OTHER INFORMATION: Synthetic DNA

<400> SEQUENCE: 22
gctccaacct ctgacctact aagaaccttt agttgtggtt tgtt              44

<210> SEQ ID NO 23
<211> LENGTH: 46
<212> TYPE: DNA
<213> ORGANISM: Artificial sequence
<220> FEATURE:
<223> OTHER INFORMATION: Synthetic DNA

<400> SEQUENCE: 23
gctccaacct ctgacctact aaaggcatag gagacaatta ggaagc            46

<210> SEQ ID NO 24
<211> LENGTH: 48
<212> TYPE: DNA
<213> ORGANISM: Artificial sequence
<220> FEATURE:
<223> OTHER INFORMATION: Synthetic DNA

<400> SEQUENCE: 24
ggtcactgtc acgagggata tcaaaggcat aggagacaat taggaaga          48

<210> SEQ ID NO 25
<211> LENGTH: 41
<212> TYPE: DNA
<213> ORGANISM: Artificial sequence
<220> FEATURE:
<223> OTHER INFORMATION: Synthetic DNA

<400> SEQUENCE: 25
gctccaacct ctgacctact aaccttcctc tcttgggacc g                 41

<210> SEQ ID NO 26
<211> LENGTH: 40
<212> TYPE: DNA
<213> ORGANISM: Artificial sequence
<220> FEATURE:
<223> OTHER INFORMATION: Synthetic DNA

<400> SEQUENCE: 26
ggtcactgtc acgagggata tccttcctct cttgggacca                   40

<210> SEQ ID NO 27
<211> LENGTH: 40
<212> TYPE: DNA
<213> ORGANISM: Artificial sequence
<220> FEATURE:
<223> OTHER INFORMATION: Synthetic DNA

<400> SEQUENCE: 27
ggtcactgtc acgagggata tggacctggc caggcattaa                   40

<210> SEQ ID NO 28
<211> LENGTH: 40
<212> TYPE: DNA
<213> ORGANISM: Artificial sequence
<220> FEATURE:
<223> OTHER INFORMATION: Synthetic DNA

<400> SEQUENCE: 28
gctccaacct ctgacctact aagacctggc caggcattac         40

<210> SEQ ID NO 29
<211> LENGTH: 52
<212> TYPE: DNA
<213> ORGANISM: Artificial sequence
<220> FEATURE:
<223> OTHER INFORMATION: Synthetic DNA

<400> SEQUENCE: 29
ggtcactgtc acgagggata tgcaaataat ttatagagaa cctagtgtga at         52

<210> SEQ ID NO 30
<211> LENGTH: 52
<212> TYPE: DNA
<213> ORGANISM: Artificial sequence
<220> FEATURE:
<223> OTHER INFORMATION: Synthetic DNA

<400> SEQUENCE: 30
gctccaacct ctgacctact aacaaataat ttatagagaa cctagtgtga ac         52

<210> SEQ ID NO 31
<211> LENGTH: 43
<212> TYPE: DNA
<213> ORGANISM: Artificial sequence
<220> FEATURE:
<223> OTHER INFORMATION: Synthetic DNA

<400> SEQUENCE: 31
ggtcactgtc acgagggata tcctgggaaa gaaaagggtt gag         43

<210> SEQ ID NO 32
<211> LENGTH: 46
<212> TYPE: DNA
<213> ORGANISM: Artificial sequence
<220> FEATURE:
<223> OTHER INFORMATION: Synthetic DNA

<400> SEQUENCE: 32
gctccaacct ctgacctact aactcctggg aaagaaaagg gttgaa         46

<210> SEQ ID NO 33
<211> LENGTH: 50
<212> TYPE: DNA
<213> ORGANISM: Artificial sequence
<220> FEATURE:
<223> OTHER INFORMATION: Synthetic DNA

<400> SEQUENCE: 33
tgcgactaag aacgctatca ggtagcagaa ggcgaaataa ttcataatta         50

<210> SEQ ID NO 34
<211> LENGTH: 50
<212> TYPE: DNA
<213> ORGANISM: Artificial sequence
<220> FEATURE:

<223> OTHER INFORMATION: Synthetic DNA

<400> SEQUENCE: 34
caagtgatcc gagaggttga agtagcagaa ggcgaaataa ttcataattc       50

<210> SEQ ID NO 35
<211> LENGTH: 46
<212> TYPE: DNA
<213> ORGANISM: Artificial sequence
<220> FEATURE:
<223> OTHER INFORMATION: Synthetic DNA

<400> SEQUENCE: 35
tgcgactaag aacgctatca gcatctctaa gctgtatgtg tgagca          46

<210> SEQ ID NO 36
<211> LENGTH: 45
<212> TYPE: DNA
<213> ORGANISM: Artificial sequence
<220> FEATURE:
<223> OTHER INFORMATION: Synthetic DNA

<400> SEQUENCE: 36
caagtgatcc gagaggttga aatctctaag ctgtatgtgt gagcg           45

<210> SEQ ID NO 37
<211> LENGTH: 25
<212> TYPE: DNA
<213> ORGANISM: Artificial sequence
<220> FEATURE:
<223> OTHER INFORMATION: Synthetic DNA

<400> SEQUENCE: 37
gtctctgaag tcaacctcac cagaa                                 25

<210> SEQ ID NO 38
<211> LENGTH: 25
<212> TYPE: DNA
<213> ORGANISM: Artificial sequence
<220> FEATURE:
<223> OTHER INFORMATION: Synthetic DNA

<400> SEQUENCE: 38
gctagtcaga caagtgacag ggaat                                 25

<210> SEQ ID NO 39
<211> LENGTH: 22
<212> TYPE: DNA
<213> ORGANISM: Artificial sequence
<220> FEATURE:
<223> OTHER INFORMATION: Synthetic DNA

<400> SEQUENCE: 39
ttgtgcaccc acactgggag ct                                    22

<210> SEQ ID NO 40
<211> LENGTH: 29
<212> TYPE: DNA
<213> ORGANISM: Artificial sequence
<220> FEATURE:
<223> OTHER INFORMATION: Synthetic DNA

<400> SEQUENCE: 40
gtatagcttg ccaaaagtag gtacttcaa                             29

<210> SEQ ID NO 41
<211> LENGTH: 29
<212> TYPE: DNA
<213> ORGANISM: Artificial sequence
<220> FEATURE:
<223> OTHER INFORMATION: Synthetic DNA

<400> SEQUENCE: 41
gcactcagaa aactcactga aaggttatt                              29

<210> SEQ ID NO 42
<211> LENGTH: 28
<212> TYPE: DNA
<213> ORGANISM: Artificial sequence
<220> FEATURE:
<223> OTHER INFORMATION: Synthetic DNA

<400> SEQUENCE: 42
ttgccttcca aagatggttc atggaatt                               28

<210> SEQ ID NO 43
<211> LENGTH: 25
<212> TYPE: DNA
<213> ORGANISM: Artificial sequence
<220> FEATURE:
<223> OTHER INFORMATION: Synthetic DNA

<400> SEQUENCE: 43
cctgaaggaa tatccaccct gcaaa                                  25

<210> SEQ ID NO 44
<211> LENGTH: 28
<212> TYPE: DNA
<213> ORGANISM: Artificial sequence
<220> FEATURE:
<223> OTHER INFORMATION: Synthetic DNA

<400> SEQUENCE: 44
agaaggaaaa gtggcagagt ttggaaat                               28

<210> SEQ ID NO 45
<211> LENGTH: 30
<212> TYPE: DNA
<213> ORGANISM: Artificial sequence
<220> FEATURE:
<223> OTHER INFORMATION: Synthetic DNA

<400> SEQUENCE: 45
actgcttaaa gttctaaacc aatcaacaat                             30

<210> SEQ ID NO 46
<211> LENGTH: 20
<212> TYPE: DNA
<213> ORGANISM: Artificial sequence
<220> FEATURE:
<223> OTHER INFORMATION: Synthetic DNA

<400> SEQUENCE: 46
aggatgaagt ggcaggggac                                        20

<210> SEQ ID NO 47
<211> LENGTH: 20
<212> TYPE: DNA
<213> ORGANISM: Artificial sequence
<220> FEATURE:
<223> OTHER INFORMATION: Synthetic DNA

```
<400> SEQUENCE: 47
caagctccca agggcatctc                                               20

<210> SEQ ID NO 48
<211> LENGTH: 28
<212> TYPE: DNA
<213> ORGANISM: Artificial sequence
<220> FEATURE:
<223> OTHER INFORMATION: Synthetic DNA

<400> SEQUENCE: 48
gcttcctgta ttccctttgt tgtctaat                                      28

<210> SEQ ID NO 49
<211> LENGTH: 25
<212> TYPE: DNA
<213> ORGANISM: Artificial sequence
<220> FEATURE:
<223> OTHER INFORMATION: Synthetic DNA

<400> SEQUENCE: 49
gccccactct caaaatctga gactt                                         25

<210> SEQ ID NO 50
<211> LENGTH: 26
<212> TYPE: DNA
<213> ORGANISM: Artificial sequence
<220> FEATURE:
<223> OTHER INFORMATION: Synthetic DNA

<400> SEQUENCE: 50
ctatctagtg gtcaccaacc tagcta                                        26

<210> SEQ ID NO 51
<211> LENGTH: 29
<212> TYPE: DNA
<213> ORGANISM: Artificial sequence
<220> FEATURE:
<223> OTHER INFORMATION: Synthetic DNA

<400> SEQUENCE: 51
gatacatcct cttacctaat ctgagctttt                                    29

<210> SEQ ID NO 52
<211> LENGTH: 37
<212> TYPE: DNA
<213> ORGANISM: Artificial sequence
<220> FEATURE:
<223> OTHER INFORMATION: Synthetic DNA

<400> SEQUENCE: 52
ccagaatcat cgtggatgcg actaagaacg ctatcag                            37

<210> SEQ ID NO 53
<211> LENGTH: 37
<212> TYPE: DNA
<213> ORGANISM: Artificial sequence
<220> FEATURE:
<223> OTHER INFORMATION: Synthetic DNA

<400> SEQUENCE: 53
taggtcgagg gatcttcaag tgatccgaga ggttgaa                            37

<210> SEQ ID NO 54
<211> LENGTH: 36
```

<212> TYPE: DNA
<213> ORGANISM: Artificial sequence
<220> FEATURE:
<223> OTHER INFORMATION: Synthetic DNA

<400> SEQUENCE: 54
gtagcacaac tcgcaggtca ctgtcacgag ggatat                                36

<210> SEQ ID NO 55
<211> LENGTH: 37
<212> TYPE: DNA
<213> ORGANISM: Artificial sequence
<220> FEATURE:
<223> OTHER INFORMATION: Synthetic DNA

<400> SEQUENCE: 55
gtatggtttc ccgctgctcc aacctctgac ctactaa                               37

<210> SEQ ID NO 56
<211> LENGTH: 36
<212> TYPE: DNA
<213> ORGANISM: Artificial sequence
<220> FEATURE:
<223> OTHER INFORMATION: Synthetic DNA

<400> SEQUENCE: 56
atagcacaac tcgcaggtca ctgtcacgag ggatat                                36

<210> SEQ ID NO 57
<211> LENGTH: 37
<212> TYPE: DNA
<213> ORGANISM: Artificial sequence
<220> FEATURE:
<223> OTHER INFORMATION: Synthetic DNA

<400> SEQUENCE: 57
gtagcacaac tcgcagctcc aacctctgac ctactaa                               37

<210> SEQ ID NO 58
<211> LENGTH: 36
<212> TYPE: DNA
<213> ORGANISM: Artificial sequence
<220> FEATURE:
<223> OTHER INFORMATION: Synthetic DNA

<400> SEQUENCE: 58
gtatggtttc ccgctggtca ctgtcacgag ggatat                                36

<210> SEQ ID NO 59
<211> LENGTH: 16
<212> TYPE: DNA
<213> ORGANISM: Artificial sequence
<220> FEATURE:
<223> OTHER INFORMATION: Synthetic DNA

<400> SEQUENCE: 59
tccacgatga ttctgg                                                      16

<210> SEQ ID NO 60
<211> LENGTH: 16
<212> TYPE: DNA
<213> ORGANISM: Artificial sequence
<220> FEATURE:
<223> OTHER INFORMATION: Synthetic DNA

<400> SEQUENCE: 60
aagatccctc gaccta                                                    16

<210> SEQ ID NO 61
<211> LENGTH: 15
<212> TYPE: DNA
<213> ORGANISM: Artificial sequence
<220> FEATURE:
<223> OTHER INFORMATION: Synthetic DNA

<400> SEQUENCE: 61
tgcgagttgt gctac                                                     15

<210> SEQ ID NO 62
<211> LENGTH: 15
<212> TYPE: DNA
<213> ORGANISM: Artificial sequence
<220> FEATURE:
<223> OTHER INFORMATION: Synthetic DNA

<400> SEQUENCE: 62
agcgggaaac catac                                                     15

<210> SEQ ID NO 63
<211> LENGTH: 19
<212> TYPE: DNA
<213> ORGANISM: Artificial sequence
<220> FEATURE:
<223> OTHER INFORMATION: Synthetic DNA

<400> SEQUENCE: 63
gacctgcgag ttgtgctac                                                 19

<210> SEQ ID NO 64
<211> LENGTH: 19
<212> TYPE: DNA
<213> ORGANISM: Artificial sequence
<220> FEATURE:
<223> OTHER INFORMATION: Synthetic DNA

<400> SEQUENCE: 64
gagcagcggg aaaccatac                                                 19

<210> SEQ ID NO 65
<211> LENGTH: 19
<212> TYPE: DNA
<213> ORGANISM: Artificial sequence
<220> FEATURE:
<223> OTHER INFORMATION: Synthetic DNA

<400> SEQUENCE: 65
ccggtgcgag ttgtgctac                                                 19

<210> SEQ ID NO 66
<211> LENGTH: 19
<212> TYPE: DNA
<213> ORGANISM: Artificial sequence
<220> FEATURE:
<223> OTHER INFORMATION: Synthetic DNA

<400> SEQUENCE: 66
cccgagcggg aaaccatac                                                 19

<210> SEQ ID NO 67
<211> LENGTH: 18
<212> TYPE: DNA
<213> ORGANISM: Artificial sequence -continued

```
<220> FEATURE:
<223> OTHER INFORMATION: Synthetic DNA

<400> SEQUENCE: 67
gctgcgggtt gtgctgcc                                              18

<210> SEQ ID NO 68
<211> LENGTH: 17
<212> TYPE: DNA
<213> ORGANISM: Artificial sequence
<220> FEATURE:
<223> OTHER INFORMATION: Synthetic DNA

<400> SEQUENCE: 68
ccggcgggaa accgtgc                                               17

<210> SEQ ID NO 69
<211> LENGTH: 19
<212> TYPE: DNA
<213> ORGANISM: Artificial sequence
<220> FEATURE:
<223> OTHER INFORMATION: Synthetic DNA

<400> SEQUENCE: 69
ccggtgcgag ttgtgctat                                             19

<210> SEQ ID NO 70
<211> LENGTH: 19
<212> TYPE: DNA
<213> ORGANISM: Artificial sequence
<220> FEATURE:
<223> OTHER INFORMATION: Synthetic DNA

<400> SEQUENCE: 70
tgcgagttgt gctatgggg                                             19

<210> SEQ ID NO 71
<211> LENGTH: 20
<212> TYPE: DNA
<213> ORGANISM: Artificial sequence
<220> FEATURE:
<223> OTHER INFORMATION: Synthetic DNA

<400> SEQUENCE: 71
gcggtccacg atgattctgg                                            20

<210> SEQ ID NO 72
<211> LENGTH: 20
<212> TYPE: DNA
<213> ORGANISM: Artificial sequence
<220> FEATURE:
<223> OTHER INFORMATION: Synthetic DNA

<400> SEQUENCE: 72
gcccaagatc cctcgaccta                                            20
```